US006875764B1

(12) United States Patent
Muzi et al.

(10) Patent No.: US 6,875,764 B1
(45) Date of Patent: Apr. 5, 2005

(54) UREA AND THIOUREA COMPOUNDS USEFUL FOR TREATMENT OF COCCIDIOSIS

(75) Inventors: Sabrina Muzi, Lund (SE); Shoaá Abdul Rahman, Lund (SE)

(73) Assignee: New Pharma Research Sweden AB, Lund (SE)

( * ) Notice: Subject to any disclaimer, the term of this patent is extended or adjusted under 35 U.S.C. 154(b) by 119 days.

(21) Appl. No.: 10/111,376

(22) PCT Filed: Oct. 27, 2000

(86) PCT No.: PCT/SE00/02091

§ 371 (c)(1),
(2), (4) Date: Jun. 7, 2002

(87) PCT Pub. No.: WO01/30749

PCT Pub. Date: May 3, 2001

(30) Foreign Application Priority Data

Oct. 28, 1999 (SE) .............................................. 9903894

(51) Int. Cl.[7] ..................... C07D 275/28; C07D 277/82; C07D 295/16; A61K 31/17; A61K 31/425
(52) U.S. Cl. ................................ 514/235.8; 514/237.2; 514/238.2; 514/255.05; 514/313; 514/332; 514/333; 514/353; 514/367; 514/412; 514/512; 514/562; 514/564; 514/566; 544/120; 544/124; 544/165; 544/167; 544/357; 544/405; 546/163; 546/256; 546/265; 546/306; 548/163; 548/515; 562/430; 562/499; 562/504; 564/43
(58) Field of Search .................................. 544/120, 124, 544/165, 167, 357, 405; 546/163, 256, 265, 306; 548/163, 515; 562/430, 504, 499; 564/43; 514/235.8, 237.2, 238.2, 255.05, 313, 332, 333, 353, 367, 412, 512, 562, 564, 566, 237, 255

(56) References Cited

U.S. PATENT DOCUMENTS

| | | | |
|---|---|---|---|
| 3,284,433 A | 11/1966 | Becker et al. | |
| 3,647,819 A | 3/1972 | Kirchner et al. | |
| 3,711,610 A | 1/1973 | Kirchner | |
| 3,867,544 A | 2/1975 | Stevenson | |
| 4,659,708 A | 4/1987 | Werbel et al. | |

FOREIGN PATENT DOCUMENTS

| | | |
|---|---|---|
| DE | 1 802 739 | 6/1969 |
| DE | 23 34 355 | 1/1975 |
| EP | 0 597 304 A1 | 5/1994 |
| WO | WO 83/00625 | 3/1983 |
| WO | WO 94/06280 | 3/1994 |
| WO | WO 95/24900 | 9/1995 |

OTHER PUBLICATIONS

Parasitology: Parasitic Protozoa text, The Parasitology Group at Aberystwyth University, 2003. (http://www.aber.ac.uk/~mpgwww/Edu/ParProto/ProtoTxt.html).*
Parasitic Diseases, The Merck Veterinary Manual, 2003. (http://www.merckvetmanual.com/mvm/index.jsp?cfile=htm/bc/170709.htm).*
Skin Disorders, The Pet Health Clinic, 2004. (http://pethealthclinic.tripod.com/skin/).*
Parasitic Flukes and Worms, Anti–Parasite.com, 2000. (http://www.anti-parasite.com/wrmsflks.html).*
International, file CAPLUS, CAPLUS accession No. 1978: 508749, Document No. 89: 108749, Meija Seika Kaisha, Ltd., "Arylthiourea derivatives for treatment of coccidiosis"; & JP, A2, 53034928, Mar. 31, 1978.
International, file CAPLUS, CAPLUS accession No. 1987: 32620, Document No. 1987: 32620, Instytut Przemyslu Farmaceutycznego, Pol., "p–Substituted derivatives of N,N'–diphenylurea"; & PL, B1, 126634, Aug. 31, 1983.
International, file CAPLUS, CAPLUS accession No. 1991: 574133, Document No. 115: 174133, Zahner, H. et al.: "Antifilarial efficacy in vitro of 2–tert–butylbenzothiazole derivatives on adult Litomosoides carinii"; & Arzneim.–Forsch. (1991), 41(8), 821–7.

\* cited by examiner

*Primary Examiner*—Deepak Rao
(74) *Attorney, Agent, or Firm*—Burns, Doane, Swecker & Mathis, LLP

(57) ABSTRACT

The present invention relates to novel compounds, pharmaceutical compositions containing the same as well as a method for treatment of parasitic disorders, wherein said compounds are administered. The present compounds are especially well suited for treatment of coccidiosis, particularly in poultry, and they have general formula (I):

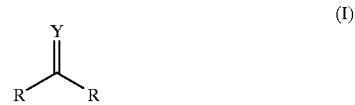

(I)

where Y is S or O and R is as defined in the specification.

12 Claims, No Drawings

UREA AND THIOUREA COMPOUNDS USEFUL FOR TREATMENT OF COCCIDIOSIS

This application is a 371 of PCT(SE00/02091 filed Oct. 27, 2000.

FIELD OF THE INVENTION

The present invention relates to novel compounds, pharmaceutical compositions containing the same as well as a method for treatment of parasitic disorders, wherein said compounds are administered.

BACKGROUND OF THE INVENTION

The coccidia are intracellular protozoan parasites which are prevalent in all domestic animals as well as in man. They are the cause of coccidiosis, which is characterized by enteritis. Coccidia of the genus *Eimeria* cause severe intestinal infections in poultry and ruminants (cattle, sheep e.t.c.). In fact, coccidiosis is one of the most-frequently occurring diseases of poultry (see inter alia "Poultry Diseases" by Jordan, F. T. W. and Pattison, M., 4$^{th}$ ed., pp. 261–276, 1996, W. B. Saunders Co. Ltd., London, UK). It deserves mentioning that the annual costs for anticoccidial medication is about £5 million in the UK only. In poultry, most cases of coccidiosis are caused by protozoa belonging to the genus *Eimeria*, such as e.g. *E. maxima, E. tenella, E. acervulina, E. necatrix, E. hagani, E. praecox, E. mitis* and *E. brunetti*. Other examples of infectious *Eimeria* protozoa are *E. gallopavonis, E. meleagrimitis, E. adenoeides, E. meleagridis, E. dispersa, E. innocua, E. subrotunda, E. truncata, E. anseris, E. bovis, E. zurnii, E. alabamansis, E. auburnensis, E. ashsata, E. parva, E. faurei, E. arloingi, E. debliecki* and *E. spinosa*.

In poultry, e.g. chickens and turkeys, an outbreak of coccidiosis may with little or no forewarning lead to a serious infection, and unless the birds are promptly treated, the result may be a very high mortality. Animals that survive these types of infections are usually of reduced economical value, since they become less efficient in converting feed to weight gain, grow much more slowly than normal animals and frequently appear listless. A similar disease scenario may also occur upon coccidia infection of larger animals, e.g. ruminants and pigs, albeit the problem is in general more severe in poultry.

In the treatment of coccidiosis, a recognized problem is the development of resistance to known anticoccidial agents. This problem has been addressed in numerous publications, such as in Stephen B. et al., *Vet. Parasitol.,* 69(1–2), pp 19–29, 1997. Indeed, there is a strong and ongoing demand in the art for both new and improved antiparasitic compounds, particularly for the treatment of coccidiosis.

As relevant prior art mention can be made of U.S. Pat. No. 5,776,982, EP 0 015 110 and U.S. Pat. No. 4,486,439, which disclose compounds useful for treatment of coccidiosis. However, none of these documents specifically discloses or suggests the compounds of the present invention.

DISCLOSURE OF THE INVENTION

There are now provided novel compounds which surprisingly have efficient antiparasitic properties. Furthermore, the present novel compounds are especially well suited for treatment of coccidiosis (vide infra). More specifically, the present invention relates to a compound having the general formula (I):

(I)

wherein
Y is selected from O and S;
R is selected from a group of substituents (a)-(c) consisting of
(a) NHR$_1$ and NHR$_2$, wherein R$_1$ and R$_2$ are selected from aryl, optionally having a straight chain, branched or cyclic saturated or unsaturated alkyl, hydroxy-alkyl or alkylamine substituent having 1–6 carbon atoms, and at least one of a group of substituents (d)–(k) consisting of
(d) aryl having at least one electron-withdrawing substituent selected from CN, NO$_2$, CF$_3$, SO$_3$H, OCN, OH, NCO, COOH, CHO, halogen, carbohydrate unit, CH(OH)A, OA, C(O)OA, C(O)A, OC(O)A, S(O)$_{0-2}$A, S(O)$_{0-2}$NHA, NHC(O)A, NHC(S)A, NHC(O)NHA, NHC(S)NHA, NHS(O)$_{o2}$A, NHS(O)$_{0-2}$NHA, C(O)NH$_{0-2}$A$_{0-2}$, C(S)NH$_{0-2}$A$_{0-2}$ and C(S)N(SO$_2$A)$_{1-2}$H$_{0-1}$A$_{0-1}$
wherein A is selected from alkyl, alkenyl, cycloalkyl and aryl, optionally having at least one of said electron-withdrawing substituents and/or containing at least one heteroatom selected from N, S and/or O;
(e) aralkyl, where at least one of the alkyl and aryl moieties have at least one electron-withdrawing substituent as defined in (d);
(f) alkyl having at least one electron-withdrawing substituent as defined in (d);
(g) condensed aryl or diphenyl, optionally having at least one heteroatom selected from N, S and/or O;
(h) cycloalkyl or alkylcycloalkyl;
(i) heterocycloalkyl or alkylheterocycloalkyl;
(j) heteroaryl or heteroaralkyl;
(k) C(NH)NH—Y, wherein Y is selected from CN, NO$_2$, CF$_3$, SO$_3$H, S(O)$_{0-2}$A, S(O)$_{0-2}$NHA, N═C-alkyl, N═C-aryl, N═C-alkenyl, N═C-heteroaryl, N═C-cyclo-alkyl, N═C-heterocycloalkyl, N═C-alkenylhetero-aryl, carboxyalkyl, carboxamidealkyl, alkyl-heterocycloalkyl, C(O)NH$_{0-2}$aryl$_{0-2}$, C(S)NH$_{0-2}$aryl$_{0-2}$ and cycloalkyl, alkylcycloalkyl or aralkyl substituted as defined in (e);
where the groups (g)-(k) optionally may have at least one electron-withdrawing substituent as defined in (d) and/or a straight chain, branched or cyclic saturated or unsaturated alkyl, hydroxyalkyl or alkylamine substituent; where the groups (d)–(k) optionally may have at least one substituent consisting of any one of the groups (d)–(k);
(b) NR$_3$R$_4$ and NR$_5$R$_6$, wherein R$_3$–R$_5$ are independently selected from a group of substituents (l)–(n) consisting of
(l) aryl;
(m) aralkyl;
(n) straight chain, branched or cyclic saturated or unsaturated alkyl or hydroxyalkyl having 1–6 carbon atoms;
where the groups (g)–(l) optionally may have at least one electron-withdrawing substituent as defined in (d) and/or a straight chain, branched or cyclic saturated or unsaturated alkyl, hydroxyalkyl or alkylamine substituent; and at least one of the group of substituents (d)–(k) and SO$_2$X, where X is selected from any one of the substituents (d)–(n) and a group of substituents (O)–(r) consisting of
(o) an -arylalkyl-NH$_{0-2}$Q$_{0-2}$ radical, where Q is an electron-withdrawing substituent as defined in (d);
(p) an -arylalkyl-NH$_{0-2}$T$_{0-2}$radical, where T is any one of the substituents (d)–(O);
(r) an -arylalkyl-NHC(Y)T radical, where T and Y are as defined above;
where the groups (d)–(r) optionally may have at least one substituent consisting of any one of the groups (d)–(r);
(c) NR$_3$R$_4$ as defined in (b), with the proviso that R$_4$ optionally may be hydrogen, and a radical having the general formula (II)

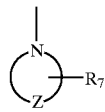

(II)

wherein Z taken together with the nitrogen atom to which it is attached forms a nitrogen-containing ring structure and R$_7$ represents at least one electron-withdrawing substituent as defined in (d);
where said nitrogen-containing ring structure optionally may have at least one substituent consisting of any one of the groups (d)–(r) and SO$_2$X;
tautomers, solvates and radiolabelled derivatives thereof; and
pharmaceutically acceptable salts thereof.

As examples of pharmaceutically acceptable salts mention can be made of acid addition salts, e.g. a salt formed by reaction with hydrohalogen acids, such as hydrochloric acid, sulphuric acid, phosphoric acid, nitric acid, aliphatic, alicyclic, aromatic or hetero-cyclic sulphonic or carboxylic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, p-hydroxybenzoic acid, embonic acid, methanesulphonic acid, ethanesulphonic acid, hydroxyethanesulphonic acid, halogenbensensulphonic acid, toluenesulphonic acid and naphthalenesulphonic acid.

In preferred embodiments of the present invention, said cycloalkyl is selected from adamantyl, cyclopropyl, cyclobutyl, cyclopentyl, cyclohexyl, hexahydrocyclopenta[c]-1H-pyrrolyl, bicyclo[2.2.1]heptanyl and 1,4-dioxaspiro[4.5]decanyl.

Moreover, said heterocycloalkyl is preferably selected from furanyl, lactonyl, lactamyl, morpholinyl, piperazinyl, piperidinyl, pyranyl, pyrrolidinyl and 4,5-dihydro-1H-imidazolyl.

Said heteroaryl is preferably selected from imidazolyl, pyridinyl, pyrazinyl, pyrimidinyl, pyrrollyl and thiazolyl.

Furthermore, said condensed aryl is preferably selected from acridinyl, anthracenyl, anthraquinonyl, benzothiazolyl, benzoxadiazolyl, indenyl, 2,3-dihydro-1H-indenyl, naphthyl, purinyl, pteridinyl, isoquinolinyl, quinolinyl, quinoxalinyl and 1,2,3,4-tetrahydro-1$\lambda^6$-thiochromenyl.

It is preferred that said nitrogen-containing ring structure is selected from acridinyl, benzothiazolyl, benzoxadiazolyl, imidazolyl, 4,5-dihydro-1H-imidazolyl, lactamyl, morpholinyl, piperazinyl, piperidinyl, purinyl, pteridinyl, pyrrolidinyl, pyridinyl, pyrazinyl, pyrimidinyl, pyrrollyl, isoquinolinyl, quinolinyl, quinoxalinyl and thiazolyl. Most preferably, said nitrogen-containing ring structure is piperazinyl.

In a more preferred embodiment of the present invention, R$_1$ and R$_2$ are not identical. In other words, this particular embodiment relates to an asymmetrically substituted urea or thiourea derivative, as is depicted in Table 1 further hereinbelow.

In another preferred embodiment, NR$_3$R$_4$ and NR$_5$R$_6$ are not identical.

In the most preferred embodiment of the present invention, at least one of R$_1$–R$_6$ is selected from 3-nitrophenyl, 4-nitrophenyl, 4-fluorophenyl, 4-cyanophenyl, 4-carboxy-2,6-diiodophenyl, 3,4-dicarboxyphenyl, 3,5-dicarboxyphenyl, 3-carboxyphenyl, 1-carboxycyclopentyl, 1-carboxycyclopropyl, 3-carboxy-2,4,5-trifluorophenyl, 4-carboxy-3-hydroxyphenyl, 3,4,5-trimethoxyphenyl, 2-(4-morpholinyl)ethyl, 2-carboxypyrimidinyl, 2-pyrazinyl, 6-chloro-2-pyrazinyl, 5-bromo-2-pyridinyl, 6-bromo-2-pyridinyl, 5-chloro-2-pyridinyl, 6-chloro-2-pyridinyl, 3-chloro-4-pyridinyl, 4,6-dihydroxy-2-pyrimidinyl, 6-nitro-1,3-benzothiazol-2-yl, carboxymethyl, 2,2,2-trifluoro-ethyl, phenylsulfonyl, (4-nitrophenyl)sulfonyl, (4-fluorophenyl) sulfonyl, (trifluoromethyl) sulfonyl, ethylsulfonyl and 2-naphthylsulfonyl.

In the very most preferred embodiment of the present invention, said compound is selected from 4-[(anilinocarbothioyl)amino]-3,5-diiodobenzoic acid; 3,5-diiodo-4-[[(4-nitrophenyl)sulfonyl]({[(4-nitrophenyl)sulfonyl]anilino}carbothioyl)amino]benzoic acid; 4-[[(4-fluorophenyl)sulfonyl]({[(4-fluorophenyl)sulfonyl]anilino}carbothioyl) amino]-3,5-diiodobenzoic acid; 4-[[(4-fluorophenyl)sulfonyl]({[(4-fluorophenyl)sulfonyl]-4-nitroanilino}carbothioyl)amino]-3,5-diiodobenzoic acid; 3,5-diiodo-4-{({4-nitro[(4-nitrophenyl)sulfonyl]anilino}-carbothioyl)[(4-nitrophenyl)sulfonyl]amino}benzoic acid; 4-{({4-fluoro[(4-nitrophenyl)sulfonyl]anilino}carbo-thioyl)[(4-nitrophenyl) sulfonyl]amino}-3,5-diiodobenzoic acid;
N$^1$, N$^4$-bis (4-nitrophenyl)-1,4-piperazinedicarbothioamide; and
4-nitro-N-{[4-({4-nitro[(4-nitrophenyl)sulfonyl]anilino}-carbothioyl)-1-piperazinyl]carbothioyl}-N-(4-nitrophenyl)benzenesulfonamide.

Furthermore, the present invention relates to a compound as set forth above for use as a pharmaceutical.

Accordingly, the present invention also relates to a pharmaceutical composition comprising a compound as set forth above as active ingredient in association with a pharmaceutically acceptable adjuvant, diluent or carrier.

Moreover, the present invention relates to an animal feed, food concentrate or drinking water comprising a compound as set forth above.

It should be noted that the composition and animal feed according to the present invention may optionally include two or more of the above outlined compounds.

In addition, the present invention relates to the use of a compound as defined above for the manufacture of a medicament for treatment of parasitic disorders, particularly coccidiosis and disorders related thereto.

The present invention is also concerned with a method for treatment of parasitic disorders, particularly coccidiosis and disorders related thereto, wherein said method comprises administering to an animal, preferably poultry, of a therapeutically effective amount of a compound as defined above.

Although the present compounds are especially suitable for treatment of coccidiodis, it is anticipated that they are also therapeutically efficient against the following protozoa, as set forth below as non-limiting examples:

*Trypanosoma* spp., such as *T. cruzi* and *T. brucei*;
*Toxoplasma*, such as *T. gondii*;
*Plasmodium*;
*Babesia* spp.;
*Theileria* spp.;
*Leishmania*, such as *L. tropica*, *L. major* and *L. donavani*;
*Entaamoeba histolytica*;
*Giardia intestinalis*;
*Hexamita meleagridis*;
*Trichomonas* spp.

The present compounds are also anticipated to be active against arthropods or helminth parasites, such as flatworms and nematodes. Typical examples of such parasites are disclosed in U.S. Pat. No. 5,863,775, the teachings of which are incorporated herein by reference.

The typical dosage of the compounds according to the present invention varies within a wide range and will depend on various factors such as the particular requirement of each receiving individual and the route of administration. The dosage is generally within the range of 0.01–1000 mg/kg animal feed or body weight.

Typical compounds according to the present invention comprised by the general formula (I) and having Y as defined above and R selected from said group (a), i.e. compounds having the following general formula (III), are depicted in Table 1 hereinbelow.

TABLE 1

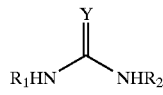

| Y | $R_1$ | $R_2$ | Denoted |
|---|---|---|---|
| S | phenyl | 6-nitro-1,3-benzothiazol-2-yl | B35 |
| O | 4-nitrophenyl | 6-nitro-1,3-benzothiazol-2-yl | B35-3 |
| S | phenyl | 3,5-dicarboxyphenyl | B37 |
| S | 4-nitrophenyl | 3,5-dicarboxyphenyl | B37-2 |
| S | 4-nitrophenyl | 6-nitro-1,3-benzothiazol-2-yl | B38 |
| S | phenyl | 5-nitro-1,3-thiazol-2-yl | B40 |
| S | phenyl | 3,4,5-trimethoxyphenyl | B41 |
| S | phenyl | 5-methyl-1,3-thiazol-2-yl | B47 |
| S | phenyl | tetrahydro-2-furanylmethyl | B48 |
| S | phenyl | 4-carboxy-2,6-diiodophenyl | B49 |
| S | 4-carboxy-2,6-diiodophenyl | carboxymethyl | B49-30 |
| S | 4-carboxy-2,6-diiodophenyl | 2,3-diiodopropyl | B49-32 |
| S | 4-cyanophenyl | phenyl | B50 |
| S | 4-cyanophenyl | 4-nitrophenyl | B51 |
| S | 4-cyanophenyl | 4-fluorophenyl | B55 |
| S | phenyl | 2-(4-morpholinyl)ethyl | B61 |
| S | 4-nitrophenyl | 2-(4-morpholinyl)ethyl | B61-2 |
| S | phenyl | 4-pyridinylmethyl | B62 |
| S | phenyl | 2-[(4-nitrophenyl)-sulfonyl]-1,3-thiazol-5-yl | B63 |
| S | 4-nitrophenyl | (2S,5R)-3,3-dimethyl-6-yl-7-oxo-4-thia-1-azabicyclo-[3.2.0]heptane-2-carboxylic acid | B300 |
| O | 4-nitrophenyl | 1-carboxycyclopentyl | B303 |
| O | 4-nitrophenyl | (4-carboxycyclohexyl)methyl | B305 |
| O | 4-nitrophenyl | 4-carboxycyclohexyl | B306 |
| O | 4-nitrophenyl | 3-carboxyphenyl | B307 |
| S | 4-nitrophenyl | 3-carboxyphenyl | B308 |
| O | 4-nitrophenyl | 4-nitro-2-(trifluoromethyl)phenyl | B311 |
| O | 4-nitrophenyl | 2-nitro-4-(trifluoromethyl)phenyl | B312 |
| O | 4-nitrophenyl | 4-chloro-3-(trifluoromethyl)phenyl | B315 |
| O | 4-nitrophenyl | 3-carboxy-2,4,5-trifluorophenyl | B316 |
| S | 4-nitrophenyl | 3-carboxy-2,4,5-trifluorophenyl | B317 |
| S | 4-nitrophenyl | 2,5-dicyano-3,4,6-trifluorophenyl | B318 |
| O | 4-nitrophenyl | 2,5-dicyano-3,4,6-trifluorophenyl | B319 |
| O | 4-nitrophenyl | 3-chloro-2,5,6-trifluoro-4-pyridinyl | B320 |
| O | 4-nitrophenyl | 2,2,2-trifluoroethyl | B321 |
| S | 4-nitrophenyl | 2,2,2-trifluoroethyl | B322 |
| O | 4-nitrophenyl | 4-(trifluoromethyl)phenyl | B326 |
| O | 4-nitrophenyl | 2-benzoyl-4-iodophenyl | B329 |
| S | 4-nitrophenyl | 2-benzoyl-4-iodophenyl | B330 |
| S | 4-nitrophenyl | 3-(4-iodophenyl)-1,4-dioxo-1,4-dihydro-2-naphthalenyl | B332 |
| O | 4-nitrophenyl | 3-(4-iodophenyl)-1,4-dioxo-1,4-dihydro-2-naphthalenyl | B333 |
| S | 4-nitrophenyl | 1-carboxy-2-(4-iodophenyl)ethyl | B334 |
| O | 4-nitrophenyl | 1-carboxy-2-(4-iodophenyl)ethyl | B335 |
| O | 4-nitrophenyl | 1-[3,4-dihydroxy-5-(hydroxymethyl)-tetrahydro-2-furanyl]-5-iodo-2-oxo-1,2-dihydro-4-pyrimidinyl | B336 |
| S | 4-nitrophenyl | 1-[3,4-dihydroxy-5-(hydroxymethyl)-tetrahydro-2-furanyl]-5-iodo-2-oxo-1,2-dihydro-4-pyrimidinyl | B337 |
| S | 4-nitrophenyl | 1-carboxy-2-[3,5-diiodo-4-(4-hydroxy-3-iodophenoxy)-phenyl]ethyl | B340 |
| O | 4-nitrophenyl | 1-carboxy-2-[3,5-diiodo-4-(4-hydroxy-3-iodophenoxy)-phenyl]ethyl | B341 |
| O | 4-nitrophenyl | 1-carboxy-2-(4-hydroxy-3-iodophenyl)-ethyl | B342 |
| S | 4-nitrophenyl | 1-carboxy-2-(4-hydroxy-3-iodophenyl)-ethyl | B343 |
| O | 4-nitrophenyl | 2-carboxy-4-iodophenyl | B344 |
| O | 4-nitrophenyl | 9-[3,4-dihydroxy-5-(iodomethyl)tetrahydro-2-furanyl]-9H-purin-6-yl | B345 |
| S | 4-nitrophenyl | 9-[3,4-dihydroxy-5-(iodomethyl)tetrahydro-2-furanyl]-9H-purin-6-yl | B346 |
| O | 4-nitrophenyl | 2-carboxy-3,5,6-trichloro-4-pyridinyl | B347 |
| O | 4-nitrophenyl | 2-carboxy-3-quinoxalinyl | B348 |
| O | 4-nitrophenyl | 2-carboxy-4-quinolinyl | B349 |
| S | 4-nitrophenyl | 2-carboxy-4-quinolinyl | B350 |
| S | 4-nitrophenyl | 2-carboxy-pyrimidinyl | B351 |
| S | 4-nitrophenyl | 3-yl-bicyclo-[2.2.1]heptane-2-carboxylic acid | B352 |

TABLE 1-continued (III)

$$R_1HN-C(=Y)-NHR_2$$

| Y | R₁ | R₂ | Denoted |
|---|---|---|---|
| S | 4-nitrophenyl | (4-carboxycyclohexyl)methyl | B354 |
| S | 4-nitrophenyl | 3-carboxy-5-hydroxypyrimidinyl | B356 |
| S | 4-nitrophenyl | 3-carboxy-4-chloropyrimidinyl | B357 |
| O | 4-nitrophenyl | 2-carboxy-9,10-dioxo-9,10-dihydro-1-anthracenyl | B358 |
| O | 4-nitrophenyl | 3-carboxyadamantyl | B359 |
| O | 4-nitrophenyl | (1S,3R)-1-yl-1,3-cyclopentane-dicarboxylic acid | B361 |
| O | 4-nitrophenyl | 2-carboxy-5-ethyl-thiopyrimidinyl | B362 |
| O | 4-nitrophenyl | 1,3,3-tricarboxypropyl | B363 |
| O | 4-nitrophenyl | 2-carboxypyrazinyl | B364 |
| O | 4-nitrophenyl | 1-carboxycyclopropyl | B368 |
| S | 4-nitrophenyl | 1-carboxycyclopropyl | B369 |
| O | 4-nitrophenyl | 2-[2,3,4-trihydroxy-1-(1-yl-2-oxoethyl)-butoxy]propanoic acid | B601 |
| O | 4-nitrophenyl | 4-oxo-6-[(1R,2S)-1,2,3-trihydroxy-propyl]-4,8-dihydro-2-pteridinyl | B602 |
| O | 4-nitrophenyl | 2,4,5-trihydroxyphenethyl | B604 |
| O | 4-nitrophenyl | 4-carboxy-2,6-dioxo-1,2,3,6-tetrahydro-5-pyrimidinyl | B606 |
| O | 4-nitrophenyl | 1,3-dihydroxy-9,10-dioxo-9,10-dihydro-2-sulfoxy-4-anthracenyl | B607 |
| O | 4-nitrophenyl | 1-carboxy-2-(2,4,5-trihydroxyphenyl)ethyl | B608 |
| O | 4-nitrophenyl | 1-[3,4-dihydroxy-5-(hydroxymethyl)-tetrahydro-2-furanyl]-6-oxo-1,6-dihydro-4-pyrimidinyl | B609 |
| O | 4-nitrophenyl | (1R,2S)-2-(3,4-dihydroxyphenyl)-2-hydroxy-1-methylethyl | B610 |
| O | 4-nitrophenyl | 3,4-dihydroxybenzyl | B611 |
| O | 4-nitrophenyl | 1-[3,4-dihydroxy-5-(hydroxymethyl)-tetrahydro-2-furanyl]-5-methyl-2-oxo-1,2-dihydro-4-pyrimidinyl | B612 |
| O | 4-nitrophenyl | 1-[3,4-dihydroxy-5-(hydroxymethyl)tetrahydro-2-furanyl]-2-thioxo-1,2-dihydro-4-pyrimidinyl | B613 |
| O | 4-nitrophenyl | 1-[3,4-dihydroxy-5-(hydroxymethyl)tetrahydro-2-furanyl]-2-oxo-1,2-dihydro-4-pyrimidinyl | B614 |
| O | 4-nitrophenyl | 4,5-dihydroxy-7-{[(4-nitroanilino)-carbonyl]amino}-9,10-dioxo-9,10-dihydro-2-anthracenyl | B615 |
| O | 4-nitrophenyl | 3,4-dihydroxyphenethyl | B616 |
| O | 4-nitrophenyl | 2-(3,4-dihydroxyphenyl)-2-hydroxyethyl | B617 |
| O | 4-nitrophenyl | 1,3-dicarboxycyclobutyl | B619 |
| O | 4-nitrophenyl | (1R,3R)-1-yl-1,3-cyclopentane-dicarboxylic acid | B620 |
| O | 4-nitrophenyl | 2-(2-carboxybenzoyl)-phenyl | B621 |
| O | 4-nitrophenyl | 5-carboxy-2-pyridinyl | B622 |
| O | 4-nitrophenyl | 1-carboxycyclohexyl | B623 |
| O | 4-nitrophenyl | 2-yl-bicyclo-[2.2.1]heptane-2-carboxylic acid | B624 |
| O | 4-nitrophenyl | 2-{[(3-nitro-anilino)carbonyl]-amino}ethyl | B635 |
| S | 4-nitrophenyl | 2-{[(3-nitroanilino)-carbothioyl]amino}ethyl | B636 |
| O | 4-nitrophenyl | 4-{[(3-nitroanilino)-carbonyl}amino)butyl | B637 |
| S | 4-nitrophenyl | 4-{[(3-nitroanilino)-carbothioyl]amino}butyl | B638 |
| O | 4-nitrophenyl | 4-{[(4-nitroanilino)-carbonyl]amino}phenyl | B639 |
| S | 4-nitrophenyl | 4-{[(4-nitroanilino)-carbothioyl]amino}phenyl | B640 |
| O | 4-nitrophenyl | 5-{[(3-nitroanilino)-carbonyl]amino}pentyl | B641 |
| S | 4-nitrophenyl | 5-{[(3-nitroanilino)-carbothioyl]amino}pentyl | B642 |
| O | 4-nitrophenyl | 4'-{[(4-nitroanilino)-carbonyl]amino}-1,1'-biphen-4-yl | B643 |
| S | 4-nitrophenyl | 4'-{[(4-nitroanilino)-carbothioyl]amino}-1,1'-biphen-4-yl | B644 |
| O | 4-nitrophenyl | 4,6-dihydroxy-2-pyrimidinyl | B645 |
| S | 4-nitrophenyl | 4,6-dihydroxy-2-pyrimidinyl | B646 |
| O | 4-nitrophenyl | 3,3'-dichloro-4'-{[(4-nitroanilino)-carbonyl]amino}-1,1'-biphen-4-yl | B647 |
| S | 4-nitrophenyl | 3,3'-dichloro-4'-{[(4-nitroanilino)-carbothioyl]amino}-1,1'-biphen-4-yl | B648 |
| O | 4-nitrophenyl | 3,3'-dimethyl-4'-{[(4-nitroanilino)-carbonyl]amino}-1,1'-biphen-4-yl | B649 |
| S | 4-nitrophenyl | 3,3'-dimethyl-4'-{[(4-nitroanilino)-carbothioyl]amino}-1,1'-biphen-4-yl | B650 |
| O | 4-nitrophenyl | (4-diethylamino-1-methyl)butyl | B651 |
| S | 4-nitrophenyl | (4-diethylamino-1-methyl)butyl | B652 |
| O | 4-nitrophenyl | 6-{[(4-nitroanilino)-carbonyl]-amino}-3-acridinyl | B653 |
| S | 4-nitrophenyl | 6-{[(4-nitroanilino)-carbothioyl]-amino}-3-acridinyl | B654 |
| O | 4-nitrophenyl | 2,4-dibromo-6-{[cyclohexyl(methyl)-amino]-methyl}phenyl | B655 |
| S | 4-nitrophenyl | 2,4-dibromo-6-{[cyclohexyl(methyl)-amino]methyl}phenyl | B656 |
| O | 4-nitrophenyl | 4-(dimethylamino)phenyl | B657 |
| S | 4-nitrophenyl | 4-(dimethylamino)phenyl | B658 |
| O | 4-nitrophenyl | 6-chloro-2-pyrazinyl | B659 |
| S | 4-nitrophenyl | 6-chloro-2-pyrazinyl | B660 |

TABLE 1-continued (III)

$$R_1HN-C(=Y)-NHR_2$$

| Y | R₁ | R₂ | Denoted |
|---|---|---|---|
| O | 4-nitrophenyl | 5-chloro-2-pyridinyl | B661 |
| S | 4-nitrophenyl | 5-chloro-2-pyridinyl | B662 |
| O | 4-fluorophenyl | {2-[(E)-(2,6-dichlorophenyl)-methylidene]hydrazino}-(imino)methyl | B663 |
| S | 4-fluorophenyl | {2-[(E)-(2,6-dichlorophenyl)-methylidene]hydrazino}-(imino)methyl | B664 |
| O | 4-fluorophenyl | N-(1-acetyl)-imidoformamidyl | B665 |
| S | 4-fluorophenyl | N-(1-acetyl)-imidoformamidyl | B666 |
| O | 4-fluorophenyl | N-(2,3-dihydro-1,4-benzodioxin-2-yl-methyl)-imidoformamidyl | B667 |
| S | 4-fluorophenyl | N-(2,3-dihydro-1,4-benzodioxin-2-yl-methyl)-imidoformamidyl | B668 |
| O | 4-fluorophenyl | N-(3-methyl-2-butenyl)-imidoformamidyl | B669 |
| S | 4-fluorophenyl | N-(3-methyl-2-butenyl)-imidoformamidyl | B670 |
| O | 4-fluorophenyl | N-(1,4-dioxaspiro-(4.5)dec-2-ylmethyl)-imidoformamidyl | B671 |
| S | 4-fluorophenyl | N-(1,4-dioxaspiro-(4.5)dec-2-ylmethyl)-imidoformamidyl | B672 |
| O | 4-fluorophenyl | N-(1-(2,6-dichlorophenyl)-2-oxo-ethyl)imido-formamidyl | B673 |
| S | 4-fluorophenyl | N-(1-(2,6-dichlorophenyl)-2-oxo-ethyl)imido-formamidyl | B674 |
| S | 4-fluorophenyl | N-cyanoimido-formamidyl | B676 |
| O | 4-fluorophenyl | {[(4-fluoroanilino)-carbonyl]amino}-(imino)methyl | B677 |
| S | 4-fluorophenyl | {[(4-fluoroanilino)-carbothioyl]amino}-(imino)methyl | B678 |
| O | 4-fluorophenyl | N-{2,3,4,6-tetra-hydroxy-5-((iminomethyl)-amino)cyclohexyl}-imidoformamidyl | B679 |
| S | 4-fluorophenyl | N-{2,3,4,6-tetra-hydroxy-5-((iminomethyl)-amino)cyclohexyl}-imidoformamidyl | B680 |
| O | 4-fluorophenyl | imino(2-{(E)-3-(5-nitro-2-furyl)-1-[(E)-2-(5-nitro-2-furyl)ethenyl]-2-propenylidene}-hydrazino)methyl | B681 |
| S | 4-fluorophenyl | imino(2-{(E)-3-(5-nitro-2-furyl)-1-[(E)-2-(5-nitro-2-furyl)ethenyl]-2-propenylidene}-hydrazino)methyl | B682 |

Compound data and systematic names for the compounds presented in Table 1 are as follows:

B35 ($C_{14}H_{10}N_4O_2S_2$; Molecular weight (MW)=330.387):
N-(6-nitro-1,3-benzothiazol-2-yl)-N'-phenylthiourea;
B35-3 ($C_{14}H_9N_5S$; MW=359.318):
N-(6-nitro-1,3-benzothiazol-2-yl)-N'-(4-nitrophenyl)urea;
B37 ($C_{15}H_{12}N_2O_4S$; MW=316.333):
5-[(anilinocarbothioyl)amino]isophtalic acid;
B37-2 ($C_{15}H_{11}N_3O_6S$; MW=361.330):
5-{[(4-nitroanilino)carbothioyl]amino}isophtalic acid;
B38 ($C_{14}H_9N_5O_4S_2$; MW=375.385):
N-(6-nitro-1,3-benzothiazol-2-yl)-N'-(4-nitrophenyl)-thiourea;
B39 ($C_{14}H_9FN_4O_2S_2$; MW=348.377):
N-(4-fluorophenyl)-N'-(6-nitro-1,3-benzothiazol-2-yl) thiourea;
B40 ($C_{10}H_8N_4O_2S_2$; MW=280.328):
N-(5-nitro-1,3-thiazol-2-yl)-N'-phenylthiourea;
B41 ($C_{16}H_{18}N_2O_3S$; MW=318.392):
N-phenyl-N'-(3,4,5-trimethoxyphenyl)thiourea;
B47 ($C_{11}H_{11}N_3S_2$; MW=249.357):
N-(5-methyl-1,3-thiazol-2-yl)-N'-phenylthiourea;
B48 ($C_{12}H_{16}N_2OS$; MW=236.334):
N-phenyl-N'-(tetrahydro-2-furanylmethyl)thiourea;
B49 ($C_{14}H_{10}I_2N_2O_2S$; MW=524.116):
4-[(anilinocarbothioyl)amino]-3,5-diiodobenzoic acid;
B49-30 ($C_{10}H_8I_2N_2O_4S$; MW=506.057):
4-({[(carboxymethyl)amino]carbothioyl}amino)-3,5-diiodobenzoic acid;
B49-32 ($C_{11}H_{10}I_4N_2O_2S$; MW=741.893):
4-({[(2,3-diiodopropyl)amino]carbothioyl}amino)-3,5-diiodobenzoic acid;
B50 ($C_{14}H_{11}N_3S$; MW=253.323):
N-(4-cyanophenyl)-N'-phenylthiourea;
B51 ($C_{14}H_{10}N_4O_2S$; MW=298.321):
N-(4-cyanophenyl)-N'-(4-nitrophenyl) thiourea;
B55 ($C_{14}H_{10}FN_3S$; MW=271.314):
N-(4-cyanophenyl)-N'-(4-fluorophenyl)thiourea;
B61 ($C_{13}H_{19}N_3OS$; MW=265.376):
N-[2-(4-morpholinyl)ethyl]-N'-phenylthiourea;
B61-2 ($C_{13}H_{18}N_4O_3S$; MW=310.373):
N-[2-(4-morpholinyl)ethyl]-N'-(4-nitrophenyl) thiourea;
B62 ($C_{13}H_{13}N_3S$; MW=243.329)
N-phenyl-N'-(4-pyridinylmethyl)thiourea;
B63 ($C_{16}H_{12}N_4O_4S_3$; MW=420.489):
N-{2-[(4-nitrophenyl)sulfonyl]-1,3-thiazol-5-yl}-N'-phenylthiourea;
B300 ($C_{15}H_{16}N_4O_5S_2$; MW=396.444):
(2S,5R)-3,3-dimethyl-6-{[(4-nitroanilino)carbothioyl]amino}-7-oxo-4-thia-1-azabicyclo[3.2.0]heptane-2-carboxylic acid;
B303 ($C_{13}H_{15}N_3O_5$; MW=293.275):
1-{[(4-nitroanilino)carbonyl]amino}cyclopentanecarboxylic acid;
B305 ($C_{15}H_{19}N_3O_5$; MW=321.329):
4-({[(4-nitroanilino)carbonyl]amino}methyl)cyclohexane-carboxylic acid;
B306 ($C_{14}H_{17}N_3O_5$; MW=307.302)
4-{[(4-nitroanilino)carbonyl]amino}cyclohexanecarboxylic acid;
B307 ($C_{14}H_{11}N_3O_5$; MW=301.254)
3-{[(4-nitroanilino)carbonyl]amino}benzoic acid;
B308 ($C_{14}H_{11}N_3O_4S$; MW=317.321):
3-{[(4-nitroanilino)carbothioyl]amino}benzoic acid;
B311 ($C_{14}H_9F_3N_4O_5$; MW=370.240):
N-(4-nitrophenyl)-N'-[4-nitro-2-(trifluoromethyl)phenyl]-urea;
B312 ($C_{14}H_9F_3N_4O_5$; MW=370.240):
N-(4-nitrophenyl)-N'-[2-nitro-4-(trifluoromethyl)phenyl]-urea;
B315 ($C_{14}H_{19}ClF_3N_3O_3$; MW=359.688):
N-[4-chloro-3-(trifluoromethyl)phenyl]-N'-(nitrophenyl)-urea;
B316 ($C_{14}H_8F_3N_3O_5$; MW=355.226): 2,3,6-trifluoro-5-{[(4-nitroanilino)carbonyl]amino}-benzoic acid;

B317 ($C_{14}H_8F_3N_3O_4S$; MW=371.292):
2,3,6-trifluoro-5-{[(4-nitroanilino)carbothioyl]amino}-benzoic acid;

B318 ($C_{15}H_6F_3N_5O_2S$; MW=377.302):
N-(2,5-dicyano-3,4,6-trifluorophenyl)-N'-(4-nitrophenyl)-thiourea;

B319 ($C_{15}H_6F_3N_5O_3$; MW=361.235):
N-(2,5-dicyano-3,4,6-trifluorophenyl)-N'-(4-nitrophenyl)-urea;

B320 ($C_{12}H_6ClF_3N_4O_3$; MW=346.649):
N-(3-chloro-2,5,6-trifluoro-4-pyridinyl)-N'-(4-nitro-phenyl)urea;

B321 ($C_9H_8F_3N_3O_3$; MW=263.173):
N-(4-nitrophenyl)-N'-(2,2,2-trifluoroethyl)urea;

B322 ($C_9H_8F_3N_3O_2S$; MW=279.240):
N-(4-nitrophenyl)-N'-(2,2,2-trifluoroethyl)thiourea;

B326 ($C_{14}H_{10}F_3N_3O_3$; MW=325.243):
N-(4-nitrophenyl)-N'-[4-(trifluoromethyl)phenyl]urea;

B329 ($C_{20}H_{14}IN_3O_4$; MW=487.247):
N-(2-benzoyl-4-iodophenyl)-N'-(4-nitrophenyl)urea;

B330 ($C_{20}H_{14}IN_3O_3S$; MW=503.314):
N-(2-benzoyl-4-iodophenyl)-N'-(4-nitrophenyl)thiourea;

B332 ($C_{23}H_{14}IN_3O_4S$; MW=555.346):
N-[3-(4-iodophenyl)-1,4-dioxo-1,4-dihydro-2-naphthalen-yl]N'-(4-nitrophenyl)thiourea;

B333 ($C_{23}H_{14}IN_3O_5$; MW=539.279):
N-[3-(4-iodophenyl)-1,4-dioxo-1,4-dihydro-2-naphthalen-yl]-N'-(4-nitrophenyl)urea;

B334 ($C_{16}H_{14}IN_3O_4S$; MW=471.271):
4-iodo-N-[(4-nitroanilino)carbothioyl]phenylalanine;

B335 ($C_{16}H_{14}IN_3O_5$; MW=455.204):
4-iodo-N-[(4-nitroanilino)carbonyl]phenylalanine;

B336 ($C_{16}H_{16}IN_5O_8$; MW=533.232):
N-{1-[3,4-dihydroxy-5-(hydroxymethyl)tetrahydro-2-furanyl]-5-iodo-2-oxo-1,2-dihydro-4-pyrimidinyl}-N'-(4-nitrophenyl)urea;

B337 ($C_{16}H_{16}IN_5O_7S$; MW=549.298):
N-{1-[3,4-dihydroxy-5-(hydroxymethyl)tetrahydro-2-furanyl]-5-iodo-2-oxo-1,2-dihydro-4-pyrimidinyl}-N'-(4-nitrophenyl)thiourea;

B340 ($C_{22}H_{16}I_3N_3O_6S$; MW=831.158):
4-(4-hydroxy-3-iodophenoxy)-3,5-diiodo-N-[(4-nitroanilino)carbothioyl]phenylalanine;

B341 ($C_{22}H_{16}I_3N_3O_7$; MW=815.092):
4-(4-hydroxy-3-iodophenoxy)-3,5-diiodo-N-[(4-nitroanilino)carbonyl]phenylalanine;

B342 ($C_{16}H_{14}IN_3O_6$; MW=471.203):
4-hydroxy-3-iodo-N-[(4-nitroanilino)carbonyl]phenyl-alanine;

B343 ($C_{16}H_{14}IN_3O_5S$; MW=487.270):
3-(4-hydroxy-3-iodophenyl)-2-{[(4-nitroanilino)carbonyl]-amino}propanethioic O-acid;

B344 ($C_{14}H_{10}IN_3O_5$; MW=427.151):
5-iodo-2-{[(4-nitroanilino)carbonyl]amino}benzoic acid;

B345 ($C_{17}H_{16}IN_7O_6$; MW=541.257):
N-{9-[3,4-dihydroxy-5-(iodomethyl)tetrahydro-2-furanyl]-9H-purin-6-yl}-N'-(4-nitrophenyl)urea;

B346 ($C_{17}H_{16}IN_7O_5S$; MW=557.324):
N-{9-[3,4-dihydroxy-5-(iodomethyl)tetrahydro-2-furanyl]-9H-purin-6-yl}-N'-(4-nitrophenyl)thiourea;

B347 ($C_{13}H_7Cl_3N_4O_5$; MW=405.577):
3,5,6-trichloro-4-{[(4-nitroanilino)carbonyl]amino}-2-pyridinecarboxylic acid;

B348 ($C_{16}H_{11}N_5O_5$; MW=353.289):
3-{[(4-nitroanilino)carbonyl]amino}-2-quinoxalinecarboxylic acid;

B349 ($C_{17}H_{12}N_4O_5$; MW=352.301):
4-{[(4-nitroanilino)carbonyl]amino}-2-quinoline-carboxylic acid;

B350 ($C_{11}H_{12}N_4O_4S$; MW=368.368):
4-{[(4-nitroanilino)carbothioyl]amino}-2-quinoline-carboxylic acid;

B351 ($C_{12}H_9N_5O_4S$; MW=319.297):
4-{[(4-nitroanilino)carbothioyl]amino}-5-pyrimidine-carboxylic acid;

B352 ($C_{15}H_{17}N_3O_4S$; MW=335.379):
3-{[(4-nitroanilino)carbothioyl]amino}bicyclo[2.2.1]-heptane-2-carboxylic acid;

B354 ($C_{15}H_{19}N_3O_4S$; MW=337.395):
4-({[(4-nitroanilino)carbothioyl]amino}methyl)cyclo-hexanecarboxylic acid;

B356 ($C_{12}H_9N_5O_5S$; MW=335.297):
6-hydroxy-2-{[(4-nitroanilino)carbothioyl]amino}-4-pyrimidinecarboxylic acid;

B357 ($C_{12}H_8ClN_5O_4S$; MW=353.742):
5-chloro-2-{[(4-nitroanilino)carbothioyl]amino}-4-pyrimidinecarboxylic acid;

B358 ($C_{22}H_{13}N_3O_7$; MW=431.355):
1-{[(4-nitroanilino)carbonyl]amino}-9,10-dioxo-9,10-dihydro-2-anthracenecarboxylic acid;

B359 ($C_{18}H_{21}N_3O_7$; MW=359.377):
3-{[(4-nitroanilino)carbonyl]amino}-1-adamantane-carboxylic acid;

B361 ($C_{14}H_{15}N_3O_7S$; MW=337.285):
(1S,3R)-1-{[(4-nitroanilino)carbonyl]amino}-1,3-cyclo-pentanedicarboxylic acid;

B362 ($C_{14}H_{13}N_5O_5S$; MW=363.350):
2-(ethylsulfanyl)-4-{[(4-nitroanilino)carbonyl]amino}-5-pyrimidinecarboxylic acid;

B363 ($C_{13}H_{13}N_3O_9$; MW=355.257):
3-{[(4-nitroanilino)carbonyl]amino}-1,1,3-propanetricarboxylic acid;

B364 ($C_{12}H_9N_5O_5$; MW=303.231):
3-{[(4-nitroanilino) carbonyl]amino}-2-pyrazinecarboxylic acid;

B368 ($C_{11}H_{11}N_3O_5$; MW=265.222):
1-{[(4-nitroanilino)carbonyl]amino}cyclopropanecarboxylic acid;

B369 ($C_{11}H_{11}N_3O_4S$; MW=281.289):
1-{[(4-nitroanilino)carbothioyl]amino}cyclopropanecarboxylic acid;

B601 ($C_{16}H_{21}N_3O_{10}$; MW=415.352):
2-[2,3,4-trihydroxy-1-(1-{[(4-nitroanilino)carbonyl]-amino)-2-oxoethyl)butoxy]propanoic acid;

B602 ($C_{16}H_{15}N_7O_7$; MW=417.333):
N-(4-nitrophenyl)-N'-{4-oxo-6-[(1R,2S)-1,2,3-trihydroxy-propyl]-4,8-dihydro-2-pteridinyl}urea;

B604 ($C_{15}H_{15}N_3O_6$; MW=333.296):
N-(4-nitrophenyl)-N'-(2,4,5-trihydroxyphenethyl)urea;

B606 ($C_{12}H_9N_5O_7$; MW=335.229):
5-{[(4-nitroanilino)carbonyl]amino}-2,6-dioxo-1,2,3,6-tetrahydro-4-pyrimidinecarboxylic acid;

B607 ($C_{21}H_{13}N_3O_{10}S$; MW=499.408):
1,3-dihydroxy-4-{[(4-nitroanilino)carbonyl]amino)-9,10-dioxo-9,10-dihydro-2-anthracenesulfonic acid;

B608 ($C_{16}H_{15}N_3O_8$; MW=377.306):
2,4,5-trihydroxy-N-[(4-nitroanilino)carbonyl]phenyl-alanine;

B609 ($C_{16}H_{17}N_5O_8$; MW=407.335):
N-{1-[3,4-dihydroxy-5-(hydroxymethyl)tetrahydro-2-furanyl]-6-oxo-1,6-dihydro-4-pyrimidinyl}-N'-(4-nitro-phenyl)urea;

B610 ($C_{16}H_{17}N_3O_6$; MW=347.323):
N-[(1R,2S)-2-(3,4-dihydroxyphenyl)-2-hydroxy-1-methylethyl]-N'-(4-nitrophenyl)urea;

B611 ($C_{14}H_{13}N_3O_5$; MW=303.270):
N-(3,4-dihydroxybenzyl)-N'-(4-nitrophenyl) urea;
B612 ($C_{17}H_{19}N_5O_8$; MW=421.362):
N-}1-[3,4-dihydroxy-5-(hydroxymethyl)tetrahydro-2-furanyl]-5-methyl-2-oxo-1,2-dihydro-4-pyrimidinyl}-N'-(4-nitrophenyl)urea;
B613 ($C_{16}H_{17}N_5O_7S$; MW=423.402):
N-{1-[3,4-dihydroxy-5-(hydroxymethyl)tetrahydro-2-furanyl]-2-thioxo-1,2-dihydro-4-pyrimidinyl}-N'-(4-nitrophenyl)urea;
B614 ($C_{16}H_{17}N_5O_8$; MW=407.335):
N-{1-[3,4-dihydroxy-S-(hydroxymethyl)tetrahydro-2-furanyl]-2-oxo-1,2-dihydro-4-pyrimidinyl}-N'-(4-nitrophenyl)urea;
B615 ($C_{28}H_{18}N_6O_{10}$; MW=598.477):
N-(4,5-dihydroxy-7-{[(4-nitroanilino)carbonyl]amino}-9,10-dioxo-9,10-dihydro-2-anthracenyl)-N'-(4-nitrophenyl)urea;
B616 ($C_{15}H_{15}N_3O_5$; MW=317.297):
N-(3,4-dihydroxyphenethyl)-N'-(4-nitrophenyl)urea;
B617 ($C_{15}H_{15}N_3O_6$; MW=333.296):
N-[2-(3,4-dihydroxyphenyl)-2-hydroxyethyl]-N'-(4-nitrophenyl)urea;
B619 ($C_{13}H_{13}N_3O_7$; MW=323.258):
1-{[(4-nitroanilino)carbonyl]amino}-1,3-cyclobutanedicarboxylic acid;
B620 ($C_{14}H_{15}N_3O_7$; MW=337.285):
(1R, 3R)-1-{[(4-nitroanilino)carbonyl]amino}-1,3-cyclopentanedicarboxylic acid;
B621 ($C_{21}H_{15}N_3O_6$; MW=405.360):
2-(2-{[(4-nitroanilino)carbonyl]amino}benzoyl)benzoic acid;
B622 ($C_{13}H_{10}N_4O_5$; MW-302.242):
6-{[(4-nitroanilino)carbonyl]amino}nicotinic acid;
B623 ($C_{14}H_{17}N_3O_5$; MW=307.302):
1-{[(4-nitroanilino)carbonyl]amino}cyclohexanecarboxylic acid;
B624 ($C_{15}H_{17}N_3O_5$; MW=319.313):
2-{[(4-nitroanilino)carbonyl]amino}-bicyclo[2.2.1]-heptane-2-carboxylic acid;
B635 ($C_{16}H_{16}N_6O_6$; MW=388.335):
N'-(2-{[(3-nitroanilino)carbonyl]amino}ethyl)-N-(4-nitrophenyl)urea;
B636 ($C_{16}H_{16}N_6O_4S_2$; MW=420.468):
N'-(2-{[(3-nitroanilino)carbothioyl]amino}ethyl)-N-(4-nitrophenyl)thiourea;
B637 ($C_{18}H_{20}N_6O_6$; MW=416.388):
N'-(4-{[(3—nitroanilino)carbonyl]amino}butyl)-N-(4-nitrophenyl)urea;
B638 ($C_{18}H_{20}N_6O_4S_2$; MW=448.521):
N'-(4-{[(3-nitroanilino)carbothioyl]amino}butyl)-N-(4-nitrophenyl)thiourea;
B639 ($C_{20}H_{16}N_6O_6$; MW=436.378):
N'-(4-{[(4-nitroanilino)carbonyl]amino}phenyl)-N-(4-nitrophenyl)urea;
B640 ($C_{20}H_{16}N_6O_4S_2$; MW=468.511):
N'-(4-{[(4-nitroanilino)carbothioyl]amino}phenyl)-N-(4-nitrophenyl)thiourea;
B641 ($C_{19}H_{22}N_6O_6$; MW=430.415):
N'-(5-{[(3-nitroanilino)carbonyl]amino}pentyl)-N-(4-nitrophenyl)urea;
B642 ($C_{19}H_{22}N_6O_4S_2$; MW=462.548):
N'-(5-{[(3-nitroanilino)carbothioyl]amino}pentyl)-N-(4-nitrophenyl)thiourea;
B643 ($C_{26}H_{20}N_6O_6$; MW=512.474):
4,4'-bis{[(4-nitroanilino)carbonyl]amino}-1,1'-biphenyl;
B644 ($C_{26}H_{20}N_6O_4S_2$; MW=544.607):
4,4'-bis{[(4-nitroanilino)carbothioyl]amino}-1,1'-biphenyl;
B645 ($C_{11}H_9N_5O_5$; MW=291.220):
N-(4,5-dihydroxy-2-pyrimidinyl)-N'-(4-nitrophenyl)urea;
B646 ($C_{11}H_9N_5O_4S$; MW=307.286):
N-(4,5-dihydroxy-2-pyrimidinyl)-N'-(4-nitrophenyl)-thiourea;
B647 ($C_{26}H_{18}Cl_2N_6O_6$; MW=581.363):
3,3'-dichloro-4,4'-bis{[(4-nitroanilino)carbonyl]amino}-1,1'-biphenyl;
B648 ($C_{26}H_{18}Cl_2N_6O_4S_2$; MW=613.497):
3,3'-dichloro-4,4'-bis{[(4-nitroanilino)carbothioyl]-amino}-1,1'-biphenyl;
B649 ($C_{28}H_{24}N_6O_6$; MW=540.527):
3,3'-dimethyl-4,4'-bis{[(4-nitroanilino)carbonyl]amino}-1,1'-biphenyl;
B650 ($C_{28}H_{24}N_6O_4S_2$; MW=572.660):
3,3'-dimethyl-4,4'-bis{[(4-nitroanilino)carbothioyl]-amino}-1,1'-biphenyl;
B651 ($C_{16}H_{26}N_4O_3$; MW=322.408):
N-[4-(diethylamino)-1-methylbutyl]-N'-(4-nitrophenyl)-urea;
B652 ($C_{16}H_{26}N_4O_2S$; MW=338.469):
N-[4-(diethylamino)-1-methylbutyl]-N'-(4-nitrophenyl)-thiourea;
B653 ($C_{27}H_{19}N_7O_6$; MW=537.483):
N'-(6-{[(4-nitroanilino)carbonyl]amino}-3-acridinyl)-N-(4-nitrophenyl)urea;
B654 ($C_{27}H_{19}N_7O_4S_2$; MW=569.617):
N'-(6-{[(4-nitroanilino)carbothioyl]amino}-3-acridinyl)-N-(4-nitrophenyl)thiourea;
B655 ($C_{21}H_{24}Br_2N_4O_3$; MW=540.248):
N-(2,4-dibromo-6-{[cyclohexyl(methyl)amino]methyl}-phenyl)-N'-(4-nitrophenyl)urea;
B656 ($C_{21}H_{24}Br_2N_4O_2S$; MW=556.315):
N-(2,4-dibromo-6-{[cyclohexyl(methyl)amino]methyl}-phenyl)-N'-(4-nitrophenyl)thiourea;
B657 ($C_{15}H_{16}N_4O_3$; MW=300.313):
N-[4-(dimethylamino)phenyl]-N'-(4-nitrophenyl)urea;
B658 ($C_{15}H_{16}N_4O_2S$; MW=316.379):
N-[4-(dimethylamino)phenyl]-N'-(4-nitrophenyl)thiourea;
B659 ($C_{11}H_8ClN_5O_3$; MW=293.666):
N-(6-chloro-2-pyrazinyl)-N'-(4-nitrophenyl)urea;
B660 ($c_{11}H_8ClN_5O_2S$; MW=309.732):
N-(6-chloro-2-pyrazinyl)-N'-(4-nitrophenyl)thiourea;
B661 ($C_{12}H_9ClN_4O_3$; MW=292.678):
N-(5-chloro-2-pyridinyl)-N'-(4-nitrophenyl)urea;
B662 ($C_{12}H_9ClN_4O_2S$; MW=308.744):
N-(5-chloro-2-pyridinyl)-N'-(4-nitrophenyl)thiourea;
B663 ($C_{15}H_{12}Cl_2FN_5O$; MW=368.193):
N-[{2-[(E)-(2,6-dichlorophenyl)methylidene]hydrazino}-(imino)methyl]-N'-(4-fluorophenyl)urea;
B664 ($C_{15}H_{12}Cl_2FN_5S$; MW=384.259):
N-[{2-[(E)-(2,6-dichlorophenyl)methylidene]hydrazino}-(imino)methyl]-N'-(4-fluorophenyl)thiourea;
B665 ($C_{10}H_{11}FN_4O_3$; MW=254.218):
2-{[{[(4-fluoroanilino)carbonyl]amino}(imino)methyl]-amino}acetic acid;
B666 ($C_{10}H_{11}FN_4O_2s$; MW=270.284):
2-{[{[(4-fluoroanilino)carbothioyl]amino}(imino)methyl]amino}acetic acid;
B667 ($C_{17}H_{17}FN_4O_3$; MW=344.340):
2-({[{[(4-fluoroanilino)carbonyl]amino}(imino) methyl]-amino}methyl)-2,3-dihydro-1,4-benzodioxine;
B668 ($C_{17}H_{17}FN_4O_2S$; MW=360.407):
2-({[{[(4-fluoroanilino)carbothioyl]amino}(imino)methyl]amino}methyl)-2,3-dihydro-1,4-benzodioxine;
B669 ($C_{13}H_{17}FN_4O$; MW=264.299):

1-fluoro-4-{[({imino[(3-methyl-2-butenyl)amino]methyl}-amino)carbonyl]amino}benzene;
B670 ($C_{13}H_{17}FN_4S$; MW=280.365):
1-fluoro-4-{[({imino[(3-methyl-2-butenyl)amino]methyl}-amino)carbothioyl]amino}benzene;
B671 ($C_{17}H_{23}FN_4O_3$; MW=350.388):
2-({[{[(4-fluoroanilino)carbonyl]amino}(imino) methyl]-amino}methyl)-1,4-dioxaspiro[4.5]decane;
B672 ($C_{17}H_{23}FN_4O_2S$; MW=366.455):
2-({[{[(4-fluoroanilino)carbothioyl]amino}(imino)methyl]-amino}methyl)-1,4-dioxaspiro[4.5]decane;
B673 ($C_{16}H_{13}Cl_2FN_4O_2$; MW=383.204):
1,3-dichloro-2-(1-{[{[(4-fluoroanilino)carbonyl]amino}-(imino)methyl]amino}-2-oxoethyl)benzene;
B674 ($C_{16}H_{13}Cl_2FN_4OS$; MW=399.271):
1,3-dichloro-2-(1-{[{[(4-fluoroanilino)carbothioyl]-amino}(imino) methyl]amino}-2-oxoethyl)benzene;
B675 ($C_9H_8FN_5O$; MW=221.191):
1-[({[(cyanoamino)(imino)methyl]amino}carbonyl)amino]-4-fluorobenzene;
B676 ($C_9H_8FN_5S$; MW=237.258):
1-[({[(cyanoamino)(imino) methyl]amino}carbothioyl)amino]-4-fluorobenzene;
B677 ($C_{15}H_{13}F_2N_5O_2$; MW=333.293):
N'-[{[(4-fluoroanilino)carbonyl]amino}(imino)methyl]-N-(4-fluorophenyl)urea;
B678 ($C_{15}H_{13}F_2N_5S_2$; MW=365.426):
N'-[{[(4-fluoroanilino)carbothioyl]amino}(imino)methyl]-N-(4-fluorophenyl)thiourea;
B679 ($C_{22}H_{26}F_2N_8O_6$; MW=536.377):
1-fluoro-4-[({[[(3-{[{[(4-fluoroanilino)carbonyl]amino}-(imino)methyl]amino}-2,4,5,6-tetrahydroxycyclohexyl)-amino](imino) methyl]amino}carbonyl) amino]benzene;
B680 ($C_{22}H_{26}F_2N_8O_4S_2$; MW=568.510):
1-fluoro-4-[({[[(3-{[{[(4-fluoroanilino) carbothioyl]-amino}(imino) methyl]amino}-2,4,5,6-tetrahydroxycyclohexyl)amino](imino)methyl]amino}carbothioyl)amino]benzene;
B681 ($C_{21}H_{16}FN_7O_7$; MW=497.393):
N-(4-fluorophenyl)-N'-[imino(2-{(E)-3-(5-nitro-2-furyl)-1-[(E)-2-(5-nitro-2-furyl)ethenyl]-2-propenylidene}hydrazino)methyl]urea;
B682 ($C_{21}H_{16}FN_7O_6S$; MW=513.460):
N-(4-fluorophenyl)-N'-[imino(2-{(E)-3-(5-nitro-2-furyl)-1-[(E)-2-(5-nitro-2-furyl)ethenyl]-2-propenylidene}hydrazino)methyl]thiourea.

Other typical compounds according to the present invention are comprised by the general formula (I) and have Y as defined above and R selected from said group (b). Thus, they have the following general formula (IV), as depicted in Table 2 hereinbelow.

TABLE 2

$$R_3R_4N-\overset{Y}{C}-NR_5R_6 \quad (IV)$$

| Y | $R_3$ | $R_4/R_5$ | $R_6$ | Denoted |
|---|---|---|---|---|
| O | 4-nitro-phenyl | 5-bromo-2-pyridinyl | 6-nitro-1,3-benzothiazol-2-yl | B35-4 |
| S | 4-nitro-phenyl | 6-chloro-2-pyrazinyl | 6-nitro-1,3-benzothiazol-2-yl | B35-5 |
| O | 4-nitro-phenyl | 6-chloro-2-pyridinyl | 6-nitro-1,3-benzothiazol-2-yl | B35-6 |

TABLE 2-continued $$R_3R_4N-\overset{Y}{C}-NR_5R_6 \quad (IV)$$

| Y | $R_3$ | $R_4/R_5$ | $R_6$ | Denoted |
|---|---|---|---|---|
| S | phenyl | (4-nitrophenyl)-sulfonyl | 6-nitro-1,3-benzothiazol-2-yl | B36 |
| S | 4-nitro-phenyl | (4-nitrophenyl)-sulfonyl | 6-nitro-1,3-benzothiazol-2-yl | B36-2 |
| O | 4-nitro-phenyl | (4-nitrophenyl)-sulfonyl | 6-nitro-1,3-benzothiazol-2-yl | B36-3 |
| S | 4-nitro-phenyl | (4-nitrophenyl)-sulfonyl | 3,5-dicarboxphenyl | B37-3 |
| S | 4-fluoro-phenyl | (4-nitrophenyl)-sulfonyl | 3,5-dicarboxphenyl | B37-4 |
| S | 4-fluoro-phenyl | 5-bromo-2-pyridinyl/ 6-bromo-2-pyridinyl | 3,5-dicarboxphenyl | B37-5 |
| S | 4-fluoro-phenyl | 6-chloro-2-pyrazinyl | 3,5-dicarboxphenyl | B37-6 |
| S | 4-fluoro-phenyl | 6-chloro-2-pyridinyl | 3,5-dicarboxphenyl | B37-7 |
| S | 4-nitro-phenyl | 6-chloro-2-pyridinyl | 3,5-dicarboxphenyl | B37-8 |
| S | 4-fluoro-phenyl | (4-nitrophenyl)-sulfonyl | 6-nitro-1,3-benzothiazol-2-yl | B42 |
| S | 4-fluoro-phenyl | 6-chloro-2-pyrazinyl | 6-nitro-1,3-benzothiazol-2-yl | B42-2 |
| S | 4-fluoro-phenyl | 6-chloro-2-pyridinyl | 6-nitro-1,3-benzothiazol-2-yl | B42-3 |
| S | 3,4-dicarboxyphenyl | (4-nitrophenyl)-sulfonyl | 1,3-benzothiazol-2-yl | B42-30 |
| S | 4-[(4-carboxyanilino)-sulfonyl]-phenyl | (4-nitrophenyl)-sulfonyl | 6-nitro-1,3-benzothiazol-2-yl | B42-31 |
| S | 8-chloro-5-quinolinyl | (4-nitrophenyl)-sulfonyl | 1,3-benzothiazol-2-yl | B42-33 |
| S | 8-chloro-5-quinolinyl | (4-nitrophenyl)-sulfonyl | 8-chloro-5-quinolinyl | B42-34 |
| S | 3-chloro-4-pyridinyl | (4-fluorophenyl)-sulfonyl | 6-chloro-2-pyrazinyl | B42-35 |
| S | 3-chloro-4-pyridinyl | (4-fluorophenyl)-sulfonyl | 3-(trifluoromethyl)phenyl | B42-26 |
| S | 4-fluoro-phenyl | (4-nitrophenyl)-sulfonyl | (4-methylphenyl)-sulfonyl | B42-37 |
| S | 4-fluoro-phenyl | (4-nitrophenyl)-sulfonyl | [5-(dimethylamino)-1-naphthyl]sulfonyl | B42-38 |
| S | 4-fluoro-phenyl | (4-nitrophenyl)-sulfonyl | (7-fluoro-2,1,3-benzoxadiazol-4-yl)sulfonyl | B42-39 |
| S | 4-fluoro-phenyl | (4-nitrophenyl)-sulfonyl | 6-methyl-1,1-dioxo-1,2,3,4-tetrahydro-1$\lambda^6$-thiochromene-7-sulfonyl | B42-40 |
| S | 3-nitro-phenyl | phenylsulfonyl | 6-nitro-1,3-benzothiazol-2-yl | B43 |
| S | phenyl | (4-nitrophenyl)-sulfonyl | 4-carboxy-2,6-diiodophenyl | B49-2 |
| S | phenyl | (4-fluorophenyl)-sulfonyl | 4-carboxy-2,6-diiodophenyl | B49-3 |
| S | 4-nitro-phenyl | (4-fluorophenyl)-sulfonyl | 4-carboxy-2,6-diiodophenyl | B49-4 |
| S | 4-nitro-phenyl | (4-nitrophenyl)-sulfonyl | 4-carboxy-2,6-diiodophenyl | B49-5 |
| S | 4-fluoro-phenyl | (4-nitrophenyl)-sulfonyl | 4-carboxy-2,6-diiodophenyl | B49-6 |
| S | phenyl | 5-bromo-2-pyridinyl | 4-carboxy-2,6-diiodophenyl | B49-7 |
| S | phenyl | 6-chloro-2-pyrazinyl | 4-carboxy-2,6-diiodophenyl | B49-8 |
| S | 4-nitro-phenyl | 6-chloro-2-pyrazinyl | 4-carboxy-2,6-diiodophenyl | B49-9 |

TABLE 2-continued

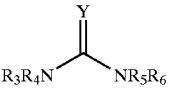

(IV)

| Y | R₃ | R₄/R₅ | R₆ | Denoted |
|---|---|---|---|---|
| S | 4-nitrophenyl | 2-pyrazinyl | 4-carboxy-2,6-diiodophenyl | B49-10 |
| S | 4-fluorophenyl | 2-pyrazinyl | 4-carboxy-2,6-diiodophenyl | B49-11 |
| S | 4-fluorophenyl | 6-chloro-2-pyrazinyl | 4-carboxy-2,6-diiodophenyl | B49-12 |
| S | 4-fluorophenyl | 6-chloro-2-pyridinyl | 4-carboxy-2,6-diiodophenyl | B49-13 |
| S | 4-nitrophenyl | 6-chloro-2-pyridinyl | 4-carboxy-2,6-diiodophenyl | B49-15 |
| S | carboxymethyl | (trifluoromethyl)sulfonyl | 4-carboxy-2,6-diiodophenyl | B49-31 |
| S | phenethyl | 2-naphthylsulfonyl | 4-carboxy-2,6-diiodophenyl | B49-33 |
| S | 4-carboxy-3-hydroxyphenyl | 2-naphthylsulfonyl | 4-carboxy-2,6-diiodophenyl | B49-34 |
| S | 2,3-diiodopropyl | (4-nitrophenyl)sulfonyl | 4-carboxy-2,6-diiodophenyl | B49-40 |
| S | 4-cyanophenyl | 6-chloro-2-pyridinyl/5-chloro-2-pyridinyl | 4-nitrophenyl | B51-2 |
| S | 4-cyanophenyl | 6-chloro-2-pyrazinyl | 4-nitrophenyl | B51-3 |
| S | 4-cyanophenyl | 5-bromo-2-pyridinyl | 4-nitrophenyl | B51-4 |
| S | 4-cyanophenyl | (4-nitrophenyl)sulfonyl | 4-nitrophenyl | B51-5 |
| S | 4-cyanophenyl | (trifluoromethyl)sulfonyl | 4-nitrophenyl | B51-6 |
| S | 4-cyanophenyl | (trifluoromethyl)sulfonyl | 4-fluorophenyl | B51-7 |
| S | phenyl | (4-nitrophenyl)sulfonyl | 3,4,5-trimethoxyphenyl | B56 |
| S | 4-nitrophenyl | (4-nitrophenyl)sulfonyl | 4-isopropylphenyl | B57 |
| S | 4-nitrophenyl | 3-chloro-2-pyridinyl | 2-(4-morpholinyl)ethyl | B61-3 |
| S | 4-nitrophenyl | 6-chloro-2-pyrazinyl | 2-(4-morpholinyl)ethyl | B61-4 |
| S | 4-nitrophenyl | (4-nitrophenyl)sulfonyl | 2-(4-morpholinyl)ethyl | B61-5 |
| S | 4-nitrophenyl | (trifluoromethyl)sulfonyl | 2-(4-morpholinyl)ethyl | B61-6 |
| O | 4-nitrophenyl | (4-nitrophenyl)sulfonyl | 1-carboxycyclopentyl | B304 |
| O | 4-nitrophenyl | (4-nitrophenyl)sulfonyl | 3-carboxyphenyl | B309 |
| O | 4-nitrophenyl | (4-nitrophenyl)sulfonyl | 2-trifluoromethyl-4-nitrophenyl | B310 |
| O | 4-nitrophenyl | (4-fluorophenyl)sulfonyl | 4-trifluoromethyl-2-nitrophenyl | B313 |
| O | 4-nitrophenyl | (4-fluorophenyl)sulfonyl | 4-chloro-3-(trifluoromethyl)phenyl | B314 |
| S | 4-nitrophenyl | 5-chloro-2-pyrazinyl/6-chloro-2-pyrazinyl | 2,2,2-trifluoroethyl | B324 |
| S | 4-nitrophenyl | (4-nitrophenyl)sulfonyl | 2,2,2-trifluoroethyl | B323 |
| O | 4-nitrophenyl | 5-chloro-2-pyrazinyl/6-chloro-2-pyrazinyl | 2,2,2-trifluoroethyl | B325 |
| O | 4-nitrophenyl | ethylsulfonyl | 4-(trifluoromethyl)phenyl | B327 |
| O | 4-nitrophenyl | 6-chloro-2-pyrazinyl | 4-(trifluoromethyl)phenyl | B328 |
| S | 4-nitrophenyl | (4-nitrophenyl)sulfonyl | 1-(3,4-dihydroxy-5-(hydroxymethyl)-tetrahydro-2-furanyl)-5-iodo-2(1H)-3-pyrimidinyl | B338 |
| S | 4-nitrophenyl | 6-chloro-2-pyrazinyl | 1-[3,4-dihydroxy-5-(hydroxymethyl)-tetrahydro-2-furanyl]-5-iodo-2-oxo-1,2-dihydro-4-pyrimidinyl | B339 |
| S | 4-nitrophenyl | (trifluoromethyl)sulfonyl | 2-carboxybicyclo[2.2.1]heptanyl | B353 |
| O | 4-nitrophenyl | 6-chloro-2-pyrazinyl | (4-carboxycyclohexyl)methyl | B355 |
| O | 4-nitrophenyl | (4-nitrophenyl)sulfonyl | 3-carboxyadamantyl | B360 |
| O | 4-nitrophenyl | (4-nitrophenyl)sulfonyl | 1,3,3-tricarboxypropyl | B363-2 |
| S | 4-nitrophenyl | (4-nitrophenyl)sulfonyl | 1-carboxycyclopropyl | B370 |
| O | 4-nitrophenyl | (4-nitrophenyl)sulfonyl | 1-(3,4-dihydroxy-1-(1-carboxyethyl)-butoxy)-2-oxo-ethyl | B600 |
| O | 4-nitrophenyl | (4-nitrophenyl)sulfonyl | 6-((1R,2S)-1,2,3-trihydroxypropyl)-4(8H)-2-pteridinenyl | B603 |
| O | 4-nitrophenyl | (4-nitrophenyl)sulfonyl | 2,4,5-trihydroxyphenethyl | B605 |
| S | same as R₆ | (4-nitrophenyl)sulfonyl | 3-{1-[(4-nitrophenyl)sulfonyl]-4,5-dihydro-1H-imidazol-2-yl}-phenyl | B800 |
| O | (4-methylphenyl)sulfonyl | (4-nitrophenyl)sulfonyl | hexahydrocyclopenta[c]pyrrol-2(1H)-yl | B801 |
| O | 4-nitrophenyl | (4-fluorophenyl)sulfonyl | (4-pyridinyl)sulfonyl | B802 |
| O | cyclohexyl | (4-nitrophenyl)sulfonyl | [4-(2-{(5-chloro-2-methoxybenzoyl)-[(4-nitrophenyl)-sulfonyl]amino}-ethyl)phenyl]-sulfonyl | B803 |
| O | cyclohexyl | (4-nitrophenyl)sulfonyl | 4-(2-{((5-methyl-2-pyrazinyl)carbonyl)-((4-nitrophenyl)-sulfonyl)amino}-ethyl)-benzenesulfonyl | B804 |
| O | cyclohexyl | (4-nitrophenyl)sulfonyl | (4-{2-[7-methoxy-4,4-dimethyl-1,3-dioxo-3,4-dihydro-2(1H)-isoquinolinyl]ethyl}phenyl)-sulfonyl | B805 |
| O | N-azepanyl | (4-nitrophenyl)sulfonyl | 4-(2-{((5-methyl-3-isoxazolyl)-carbonyl)((4-nitrophenyl)-sulfonyl)amino}-ethyl)-benzenesulfonyl | B806 |
| O | (4-methylphenyl)-sulfonyl | 4-nitrophenyl | 3-hydroxy-4,7,7-trimethylbicyclo[2.2.1]hept-2-yl | B807 |
| O | butyl | (4-nitrophenyl)sulfonyl | (4-{[(4-nitrophenyl)-sulfonyl]amino}-phenyl)sulfonyl | B808 |
| O | cyclohexyl | (4-nitrophenyl)sulfonyl | 2,3-dihydro-1H-inden-5-yl-sulfonyl | B809 |

TABLE 2-continued

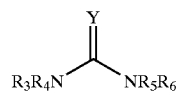

(IV)

| Y | R$_3$ | R$_4$/R$_5$ | R$_6$ | Denoted |
|---|---|---|---|---|
| O | 4-nitro-phenyl | (4-fluoro-phenyl)sulfonyl | (4-pyridinyl)sulfonyl | B810 |

Compound data and systematic names for the compounds presented in Table 2 are as follows:

B35-4 ($C_{24}H_{13}Br_2N_7O_5S$; MW=671.278):
N,N'-bis (5-bromo-2-pyridinyl)-N-(6-nitro-1,3-benzothiazol-2-yl)-N'-(4-nitrophenyl)urea;

B35-5 ($C_{22}H_{11}Cl_2N_9O_4S_2$; MW=600.418):
N,N'-bis (6-chloro-2-pyrazinyl)-N-(6-nitro-1,3-benzothiazol-2-yl)-N'-(4-nitrophenyl)thiourea;

B35-6 ($C_{24}H_{13}Cl_2N_7O_5S$; MW=582.376):
N,N'-bis(6-chloro-2-pyridinyl)-N-(6-nitro-1,3-benzothiazol-2-yl)-N'-(4-nitrophenyl)urea;

B36 ($C_{26}H_{16}N_6O_{10}S_4$; MW=700.704):
4-nitro-N-(6-nitro-1,3-benzothiazol-2-yl)-N-({[(4-nitrophenyl) sulfonyl]anilino}carbothioyl) benzenesulfonamide;

B36-2 ($C_{26}H_{15}N_7O_{12}S_4$; MW=745.701):
4-nitro-N-(6-nitro-1,3-benzothiazol-2-yl)-N-({4-nitro[(4-nitrophenyl)sulfonyl]anilino}carbothioyl) benzenesulfonamide;

B36-3 ($C_{26}H_{16}N_6O_{11}S_3$; MW=684.637):
4-nitro-N-(6-nitro-1,3-benzothiazol-2-yl)-N-({4-nitro [(4-nitrophenyl)sulfonyl]anilino}carbonyl) benzenesulfonamide;

B37-3 ($C_{27}H_{17}N_5O_{14}S_3$; MW=731.647):
5-{({4-nitro[(4-nitrophenyl)sulfonyl]anilino}carbothioyl)[(4-nitrophenyl)sulfonyl]amino}isophthalic acid;

B37-4 ($C_{27}H_{17}FN_4O_{12}S_3$; MW=704.640):
5-{({4-fluoro[(4-nitrophenyl)sulfonyl]anilino}carbothioyl)[(4-nitrophenyl)sulfonyl]amino}isophthalic acid;

B37-5 ($C_{25}H_{15}Br_2FN_4O_4S$; MW=646.284):
5-((6-bromo-2-pyridinyl){[(5-bromo-2-pyridinyl)-4-fluoroanilino]carbothioyl}amino)isophthalic acid;

B37-6 ($C_{23}H_{13}Cl_2FN_6O_4S$; MW=559.357):
5-((6-chloro-2-pyrazinyl){[(6-chloro-2-pyrazinyl)-4-fluoroanilino]carbothioyl}amino)isophthalic acid; B37-7 ($C_{25}H_{15}Cl_2FN_4O_4S$; MW=557.381):
5-((6-chloro-2-pyridinyl){[(6-chloro-2-pyridinyl)-4-fluoroanilino]carbothioyl}amino)isophthalic acid;

B37-8 ($C_{25}H_{15}Cl_2N_5O_6S$; MW=584.388):
5-((6-chloro-2-pyridinyl){[(6-chloro-2-pyridinyl)-4-nitroanilino]carbothioyl}amino)isophthalic acid;

B42 ($C_{26}H_{15}FN_6O_{10}S_4$; MW=718.694):
N-(4-fluorophenyl)-4-nitro-N-({(6-nitro-1,3-benzothiazol-2-yl)[(4-nitrophenyl)sulfonyl]amino}carbothioyl) benzene-sulfonamide;

B42-2 ($C_{22}H_{11}Cl_2FN_8O_2S_2$; MW=73.411):
N,N'-bis(6-chloro-2-pyrazinyl)-N-(4-fluorophenyl)-N'-(6-nitro-1,3-benzothiazol-2-yl)thiourea;

B42-3 ($C_{24}H_{13}Cl_2FN_6O_2S_2$; MW=571.435):
N,N'-bis(6-chloro-2-pyridinyl)-N-(4-fluorophenyl)-N'-(6-nitro-1,3-benzothiazol-2-yl)thiourea;

B42-30 ($C_{28}H_{17}N_5O_{12}S_4$; MW=743.725):
4-{({(1,3-benzothiazol-2-yl)[(4-nitrophenyl)sulfonyl]-amino}carbothioyl)[(4-nitrophenyl)sulfonyl]amino}-phthalic acid;

B42-31 ($C_{33}H_{21}N_7O_{14}S_2$; MW=899.889):
4-{[(4-{({(6-nitro-1,3-benzothiazol-2-yl)[(4-nitrophen-yl)sulfonyl]amino}carbothioyl)[(4-nitrophenyl)sulfonyl]-amino}phenyl)sulfonyl]amino}benzoic acid;

B42-33 ($C_{29}H_{17}ClN_6O_8S_4$; MW=741.198):
N-(1,3-benzothiazol-2-yl)-N-({(8-chloro-5-quinolinyl)[(4-nitrophenyl)sulfonyl]amino}carbothioyl)-4-nitro-benzenesulfonamide;

B42-34 ($C_{31}H_{18}Cl_2N_6O_8S_3$; MW=769.614):
N-(8-chloro-5-quinolinyl)-N-({(8-chloro-5-quinolinyl)[(4-nitrophenyl)sulfonyl]amino}carbothioyl)-4-nitrobenzene-sulfonamide;

B42-35 ($C_{22}H_{13}Cl_2F_2N_5O_4S_3$; MW=616.470):
N-({(6-chloro-2-pyrazinyl)[(4-fluorophenyl)sulfonyl]amino}carbothioyl)-N-(3-chloro-4-pyridinyl)-4-fluorobenzene-sulfonamide;

B42-36 ($C_{25}H_{15}ClF_3N_3O_4S_3$; MW=648.047):
N-(3-chloro-4-pyridinyl)-4-fluoro-N-{[[(4-fluorophenyl)-sulfonyl]-3-(trifluoromethyl)anilino] carbothioyl}benzene-sulfonamide;

B42-37 ($C_{26}H_{19}FN_4O_{10}S_4$; MW=694.712):
N-({4-fluoro[(4-nitrophenyl)sulfonyl]anilino}carbothioyl)-N-[(4-methylphenyl)sulfonyl]-4-nitrobenzenesulfonamide;

B42-38 ($C_{27}H_{22}FN_5O_{10}S_4$; MW=723.754):
N-{[5-(dimethylamino)-1-naphthyl]sulfonyl}-N-({4-fluoro[(4-nitrophenyl)sulfonyl]anilino}carbothioyl)-4-nitrobenzenesulfonamide;

B42-39 ($C_{25}H_{14}F_2N_6O_{11}S_4$; MW=740.673):
N-[(7-fluoro-2,1,3-benzoxadiazol-4-yl)sulfonyl]-N-({4-fluoro[(4-nitrophenyl)sulfonyl]anilino}carbothioyl)-4-nitrobenzenesulfonamide;

B42-40 ($C_{29}H_{23}FN_4O_{12}S_5$; MW=798.841):
N-({4-fluoro[(4-nitrophenyl)sulfonyl]anilino}carbothioyl)-N-[(6-methyl-1,1-dioxo-1,2,3,4-tetrahydro-1λ$^6$-thiochromen-7-yl)sulfonyl]-4-nitrobenzenesulfonamide;

B43 ($C_{26}H_{17}N_5O_8S_4$; MW=655.706):
N-{[(6-nitro-1,3-benzothiazol-2-yl) (phenylsulfonyl)amino] carbothioyl}-N-(3-nitrophenyl) benzenesulfonamide;

B49-2 ($C_{26}H_{16}I_2N_4O_{10}S_3$; MW=894.433):
3,5-diiodo-4-[[(4-nitrophenyl)sulfonyl]({[(4-nitrophenyl)sulfonyl]anilino}carbothioyl)amino]benzoic acid;

B49-3 ($C_{26}H_{16}F_2I_2N_2O_6S_3$; MW=840.419):
4-[[(4-fluorophenyl)sulfonyl]({[(4-fluorophenyl)sulfonyl]anilino}carbothioyl)amino]-3,5-diiodobenzoic acid;

B49-4 ($C_{26}H_{15}F_2I_2N_3O_8S_3$; MW=885.416):
4-[[(4-fluorophenyl)sulfonyl]({[(4-fluorophenyl)sulfonyl]-4-nitroanilino}carbothioyl)amino]-3,5-diiodobenzoic acid;

B49-5 ($C_{26}H_{15}I_2N_5O_{12}S_3$; MW=939.431):
3,5-diiodo-4-{({4-nitro[(4-nitrophenyl)sulfonyl]anilino}-carbothioyl)[(4-nitrophenyl) sulfonyl]amino}benzoic acid;

B49-6 ($C_{26}H_{15}FI_2N_4O_{10}S_3$; MW=912.424):
4-{({4-fluoro[(4-nitrophenyl)sulfonyl]anilino}carbothioyl)[(4-nitrophenyl)sulfonyl]amino}-3,5-diiodobenzoic acid;

B49-7 ($C_{24}H_{14}Br_2I_2N_4O_2S$; MW=836.077):
4-((5-bromo-2-pyridinyl){[(5-bromo-2-pyridinyl)anilino]-carbothioyl}amino)-3,5-diiodobenzoic acid;

B49-8 ($C_{22}H_{12}Cl_2I_2N_6O_2S$; MW=749.150):
4-((6-chloro-2-pyrazinyl){[(6-chloro-2-pyrazinyl)-anilino] carbothioyl}amino)-3,5-diiodobenzoic acid;

B49-9 ($C_{22}H_{11}Cl_2I_2N_7O_4S$; MW=794.148):
4-((6-chloro-2-pyrazinyl){[(6-chloro-2-pyrazinyl)-4-nitroanilino]carbothioyl}amino)-3,5-diiodobenzoic acid;

B49-10 ($C_{22}H_{13}I_2N_7O_4S$; MW=725.258):
3,5-diiodo-4-[{[4-nitro(2-pyrazinyl)anilino]carbothioyl}-(2-pyrazinyl)amino] benzoic acid;

B49-11 (C$_{22}$H$_{13}$FI$_2$N$_6$O$_2$S; MW=698.251):
4-[{[4-fluoro(2-pyrazinyl)anilino]carbothioyl}(2-pyrazinyl)
amino]-3,5-diiodobenzoic acid;

B49-12 (C$_{22}$H$_{11}$Cl$_2$FI$_2$N$_6$O$_2$S; MW=767.141):
4-((6-chloro-2-pyrazinyl){[(6-chloro-2-pyrazinyl)-4-fluoroanilino]carbothioyl}amino)-3,5-diiodobenzoic acid;

B49-13 (C$_{24}$H$_{23}$Cl$_2$FI$_2$N$_4$O$_2$S; MW=765.164):
4-((6-chloro-2-pyridinyl){[(6-chloro-2-pyridinyl)-4-fluoroanilino]carbothioyl}amino)-3,5-diiodobenzoic acid;

B49-15 (C$_{24}$H$_{13}$Cl$_2$I$_2$N$_5$O$_4$S; MW=792.172):
4-((6-chloro-2-pyridinyl){[(6-chloro-2-pyridinyl)-4-nitroanilino]carbothioyl}amino)-3,5-diiodobenzoic acid;

B49-31 (C$_{12}$H$_6$F$_6$I$_2$N$_2$O$_8$S$_3$; MW=770.182):
4-{({(carboxymethyl)[(trifluoromethyl)sulfonyl]amino}-carbothioyl)[(trifluoromethyl)sulfonyl]amino}-3,5-diiodobenzoic acid;

B49-33 (C$_{36}$H$_{26}$I$_2$N$_2$O$_6$S$_3$; MW=932.608):
3,5-diiodo-4-((2-naphthylsulfonyl){[(2-naphthylsulfonyl)-(phenethyl)amino]carbothioyl}amino)benzoic acid;

B49-34 (C$_{35}$H$_{22}$I$_2$N$_2$O$_9$S$_3$; MW=964.564):
4-[{[4-carboxy-3-hydroxy(2-naphthylsulfonyl)anilino]carbothioyl}(2-naphthylsulfonyl)amino]-3,5-diiodobenzoic acid;

B49-40 (C$_{23}$H$_{16}$I$_4$N$_4$O$_{10}$S$_3$; MW=1112.210):
4-{({(2,3-diiodopropyl)[(4-nitrophenyl)sulfonyl]amino}-carbothioyl)[(3-nitrophenyl)sulfonyl]amino}-3,5-diiodobenzoic acid;

B51-2 (C$_{24}$H$_{14}$Cl$_2$N$_6$O$_2$S; MW=521.379):
N-(5-chloro-2-pyridinyl)-N'-(6-chloro-2-pyridinyl)-N'-(4-cyanophenyl)-N-(4-nitrophenyl)thiourea;

B51-3 (C$_{22}$H$_{12}$Cl$_2$N$_8$O$_2$S; MW=523.355):
N,N'-bis(6-chloro-2-pyrazinyl)-N-(4-cyanophenyl)-N'-(4-nitrophenyl)thiourea;

B51-4 (C$_{24}$H$_{14}$Br$_2$N$_6$O$_2$S; MW=610.281):
N,N'-bis(5-bromo-2-pyridinyl)-N-(4-cyanophenyl)-N'-(4-nitrophenyl)thiourea;

B51-5 (C$_{26}$H$_{16}$N$_6$O$_{10}$S$_3$; MW=668.638):
N-({4-cyano[(4-nitrophenyl)sulfonyl]anilino}carbothioyl)-4-nitro-N-(4-nitrophenyl)benzenesulfonamide;

B51-6 (C$_{16}$H$_8$F$_6$N$_4$O$_6$S$_3$; MW=562.447):
N-(4-cyanophenyl)(trifluoro)-N-({4-nitro[(trifluoromethyl)sulfonyl]anilino}carbothioyl) methanesulfonamide;

B51-7 (C$_{16}$H$_8$F$_7$N$_3$O$_4$S$_3$; MW=535.439):
N-(4-cyanophenyl)(trifluoro)-N-({4-fluoro[(trifluoromethyl)sulfonyl]anilino}carbothioyl) methanesulfonamide;

B56 (C$_{28}$H$_{24}$N$_4$O$_{11}$S3; MW=688.708):
4-nitro-N-({[(4-nitrophenyl)sulfonyl]anilino}carbothioyl)-N-(3,4,5-trimethoxyphenyl)benzenesulfonamide;

B57 (C$_{28}$H$_{23}$N$_5$O$_{10}$S$_3$; MW=685.708):
N-({4-isopropyl[(4-nitrophenyl)sulfonyl]anilino}carbothioyl)-4-nitro-N-(4-nitrophenyl)benzenesulfonamide;

B61-3 (C$_{23}$H$_{22}$Cl$_2$N$_6$O$_3$S; MW=533.431):
N,N'-bis(3-chloro-2-pyridinyl)-N-[2-(4-morpholinyl)-ethyl]-N'-(4-nitrophenyl)thiourea;

B61-4 (C$_{21}$H$_{20}$Cl$_2$N$_8$O$_3$S; MW=535.407):
N,N'-bis(6-chloro-2-pyrazinyl)-N-[2-(4-morpholinyl)-ethyl]-N'-(4-nitrophenyl)thiourea;

B61-5 (C$_{25}$H$_{24}$N$_6$O$_{13}$S$_3$; MW=680.690):
N-[2-(4-morpholinyl)ethyl]-4-nitro-N-({4-nitro[(4-nitrophenyl)sulfonyl]anilino}carbothioyl)benzenesulfonamide;

B61-6 (C$_{15}$H$_{16}$F$_6$N$_4$O$_7$S$_3$; MW=574.499):
trifluoro-N-[2-(4-morpholinyl)ethyl]-N-({4-nitro[(trifluoromethyl)sulfonyl]anilino}carbothioyl) methanesulfonamide;

B304 (C$_{25}$H$_{23}$N$_3$O9S$_2$; MW=573.597):
1-{({4-nitro[(4-nitrophenyl)sulfonyl]anilino}carbonyl)-[(4-nitrophenyl)sulfonyl]amino}cyclopentanecarboxylic acid;

B309 (C$_{26}$H$_{17}$N$_5$O$_{13}$S$_2$; MW=671.571):
3-{({4-nitro[(4-nitrophenyl)sulfonyl]anilino}carbonyl)-[(4-nitrophenyl)sulfonyl]amino}benzoic acid;

B310 (C$_{26}$H$_{15}$F$_3$N$_6$O$_3$S$_2$; MW=740.557):
4-nitro-N-{[4-nitro[(4-nitrophenyl)sulfonyl]1-2-(trifluoromethyl)anilino]carbonyl}-N-(4-nitrophenyl)benzene-sulfonamide;

B313 (C$_{26}$H$_{15}$F$_5$N$_4$O$_9$S$_2$; MW=686.543):
4-fluoro-N-{[[(4-fluorophenyl)sulfonyl]-2-nitro-4-(trifluoromethyl)anilino]carbonyl}-N-(4-nitrophenyl)benzene-sulfonamide;

B314 (C$_{26}$H$_{15}$ClF$_5$N$_3$O$_7$S$_2$; MW=675.990):
N-{[4-chloro[(4-fluorophenyl)sulfonyl]-3-(trifluoromethyl)anilino]carbonyl}-4-fluoro-N-(4-nitrophenyl)benzene-sulfonamide;

B323 (C$_{21}$H$_{14}$F$_3$N$_5$O$_{10}$S$_3$; MW=649.557):
4-nitro-N-(4-nitrophenyl)-N-{[[(4-nitrophenyl)sulfonyl]-(2,2,2-trifluoroethyl)amino]carbotiohyl}benzenesulfonamide;

B324 (C$_{17}$H$_{10}$Cl$_2$F$_3$N$_7$O$_2$S; MW=504.274):
N-(5-chloro-2-pyrazinyl)-N'-(6-chloro-2-pyrazinyl)-N-(4-nitrophenyl)-N'-(2,2,2-trifluoroethyl)thiourea;

B325 (C$_{17}$H$_{10}$Cl$_2$F$_3$N$_7$O$_3$; MW=488.207):
N-(5-chloro-2-pyrazinyl)-N'-(6-chloro-2-pyrazinyl)-N-(4-nitrophenyl)-N'-(2,2,2-trifluoroethyl)urea;

B327 (C$_{18}$H$_{18}$F$_3$N$_3$O$_9$S$_2$; MW=509.479):
N-{[[(ethylsulfonyl)-4-nitroanilino]carbonyl}-N-[4-(trifluoromethyl)phenyl]-1-ethanesulfonamide;

B328 (C$_{22}$H$_{12}$Cl$_2$F$_3$N$_7$O$_3$; MW=550.277):
N,N'-bis (6-chloro-2-pyrazinyl)-N-(4-nitrophenyl)-N'-[4-(trifluoromethyl)phenyl]urea;

B338 (C$_{28}$H$_{22}$IN$_7$O$_{15}$S$_3$; MW=919.615):
N-({{1-[3,4-dihydroxy-5-(hydroxymethyl)tetrahydro-2-furanyl]-5-iodo-2-oxo-1,2-dihydro-4-pyrimidinyl}[(4-nitrophenyl)sulfonyl]amino}carbothioyl)-4-nitro-N-(4-nitrophenyl)benzenesulfonamide;

B339 (C$_{24}$H$_{18}$Cl$_2$N$_9$O$_7$S; MW=774.332):
N,N'-bis(6-chloro-2-pyrazinyl)-N-{1-[3,4-dihydroxy-5-(hydroxymethyl)tetrahydro-2-furanyl]-5-iodo-2-oxo-1,2-dihydro-4-pyrimidinyl}-N'-(4-nitrophenyl) thiourea;

B353 (C$_{17}$H$_{15}$F$_6$N$_3$O$_8$S$_3$; MW=599.505):
3-{({4-nitro[(trifluoromethyl)sulfonyl]anilino}carbothioyl)[(trifluoromethyl)sulfonyl]amino}bicyclo [2.2.1]-heptane-2-carboxylic acid;

B355 (C$_{23}$H$_{21}$Cl$_2$N$_7$0$_5$; MW=546.362):
4-[((6-chloro-2-pyrazinyl){[(6-chloro-2-pyrazinyl)-4-nitroanilino]carbonyl}amino)methyl]cyclohexanecarboxylic acid;

B360 (C$_{30}$H$_{27}$N$_5$O$_{13}$S$_2$; MW=729.693)
3-{({4-nitro[(3-nitrophenyl)sulfonyl]anilino}carbonyl)[(4-nitrophenyl)sulfonyl]amino}-1-adamantanecarboxylic acid;

B363-2 (C$_{25}$H$_{19}$N$_5$O$_{17}$S$_2$; MW=725.574):
3-{({4-nitro[(4-nitrophenyl)sulfonyl]anilino}carbonyl)[(4-nitrophenyl)sulfonyl]amino}-1,1,3-propanetricarboxylic acid;

B370 (C$_{23}$H$_{17}$N$_5$O$_{12}$S$_3$; MW=651.606):
1-{({4-nitro[(4-nitrophenyl)sulfonyl]anilino}carbothioyl)[(4-nitrophenyl)sulfonyl]amino}cyclopropanecarboxylic acid;

B600 (C$_{28}$H$_{27}$N$_5$O$_{17}$S$_2$; MW=769.669):
2-[3,4-dihydroxy-1-(1-{({4-nitro[(4-nitrophenyl)sulfonyl]anilino}carbonyl)[(4-nitrophenyl)sulfonyl]amino}-2-oxoethyl)butoxy]propanoic acid;

B603 ($C_{28}H_{21}N_9O_{15}S_2$; MW=787.650):
12-(4-nitrophenyl)-4,9,9,11,13,13-hexaoxo-10-{4-oxo-6-[(1R,2S)-1,2,3-trihydroxypropyl]-4,8-dihydro-2-pteridinyl}benzenesulfonamide;

B605 ($C_{27}H_{21}N_5O_{14}S_2$; MW=703.613):
4-nitro-N-({4-nitro[(4-nitrophenyl)sulfonyl]anilino}carbonyl)-N-(2,4,5-trihydroxyphenethyl)benzenesulfonamide;

B800 ($C_{43}H_{32}N_{10}O_{16}S_5$; MW=1105.102):
4-nitro-N-(3-{1-[(4-nitrophenyl)sulfonyl]-4,5-dihydro-1H-imidazol-2-yl}phenyl)-N-[([(4-nitrophenyl)sulfonyl]-3-{1-[(4-nitrophenyl)sulfonyl]-4,5-dihydro-1H-imidazol-2-yl}anilino)carbothioyl]benzenesulfonamide;

B801 ($C_{27}H_{27}N_5O_{11}S_3$; MW=693.728):
N-hexahydrocyclopenta[c]pyrrol-2(1H)-yl-N-({[(4-methylphenyl)sulfonyl][(4-nitrophenyl)sulfonyl]amino}carbonyl)-4-nitrobenzenesulfonamide;

B802 ($C_{24}H_{16}F_2N_4O_9S_3$; MW=638.600):
N-[(4-fluorophenyl)sulfonyl]-N-({[(4-fluorophenyl)sulfonyl]-4-nitroanilino}carbonyl)-4-pyridinesulfonamide;

B803 ($C_{41}H_{37}ClN_6O_{17}S_4$; MW=1049.479):
N-({{[4-(2-{(5-chloro-2-methoxybenzoyl)[(4-nitrophenyl)sulfonyl]amino}ethyl)phenyl]sulfonyl}[(4-nitrophenyl)sulfonyl]amino}carbonyl)-N-cyclohexyl-4-nitrobenzenesulfonamide;

B804 ($C_{39}H_{36}N_8O_{16}S_4$; MW=1001.011):
N-({cyclohexyl[(4-nitrophenyl)sulfonyl]amino}carbonyl)-4-(2-{[(5-methyl-2-pyrazinyl)carbonyl][(4-nitrophenyl)sulfonyl]amino}ethyl)-N-[(4-nitrophenyl)sulfonyl]benzene-sulfonamide;

B805 ($C_{39}H_{39}N_5O_{14}S_3$; MW=897.950):
N-({cyclohexyl[(4-nitrophenyl)sulfonyl]amino}carbonyl)-4-{2-[7-methoxy-4,4-dimethyl-1,3-dioxo-3,4-dihydro-2(1H)-isoquinolinyl]ethyl}-N-[(4-nitrophenyl)sulfonyl]benzene-sulfonamide;

B806 ($C_{38}H_{36}N_8O_{17}S_4$; MW=1005.000):
N-(1-azepanyl)-N-({{[4-(2-{[(5-methyl-3-isoxazolyl)carbonyl][(4-nitrophenyl)sulfonyl]amino}ethyl)phenyl]sulfonyl}[(4-nitrophenyl)sulfonyl]amino}carbonyl)-4-nitrobenzenesulfonamide;

B807 ($C_{30}H_{32}N_4O_8S$; MW=608.663):
({[(3-hydroxy-4,7,7-trimethylbicyclo[2.2.1]hept-2-yl)-4-nitroanilino]carbonyl}-4-nitroanilino)(4-methylphenyl)di-oxo-$\lambda^6$-sulfane;

B808 ($C_{29}H_{26}N_6O_{15}S_4$; MW=826.812):
N-butyl-4-nitro-N-({[(4-nitrophenyl)sulfonyl][(4-nitrophenyl)sulfonyl]amino}phenyl)sulfonyl]amino}carbonyl)-benzenesulfonamide;

B809 ($C_{28}H_{28}N_4O_{11}S_3$; MW=692.740):
N-({cyclohexyl[(4-nitrophenyl)sulfonyl]amino}carbonyl)-N-(2,3-dihydro-1H-inden-5-yl-sulfonyl)-4-nitrobenzenesulfonamide;

B810 ($C_{24}H_{16}F_2N_4O_9S_3$; MW=638.600):
N-[(4-fluorophenyl)sulfonyl]-N-({[(4-fluorophenyl)sulfonyl]-4-nitroanilino}carbonyl)-4-pyridinesulfonamide.

Some other typical compounds according to the present invention are depicted in Table 3 below. They correspond to Y as defined above and R selected from said group (c) and have the general formula (V).

TABLE 3

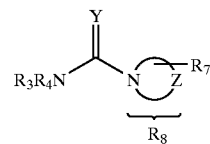

(V)

| Y | $R_3$ | $R_4$ | $R_8$ | $R_7$ (4-N-linked) | Denoted |
|---|---|---|---|---|---|
| S | 4-nitrophenyl | H | piperazin-1-yl | {[(4-nitrophenyl)-amino]carbothioyl} | B45 |
| S | 4-nitrophenyl | (4-nitrophenyl)sulfonyl | piperazin-1-yl | {[(4-nitrophenyl)[(4-nitrophenyl)sulfonyl]amino]carbothioyl} | B46 |

Compound data and systematic names for the compounds in Table 3 are as follows:

B45 ($C_{18}H_{18}N_6O_4S_2$; MW=446.506):
$N^1,N^4$-bis (4-nitrophenyl)-1,4-piperazinedicarbothioamide;

B46 ($C_{30}H_{24}N_8O_{12}S_4$; MW=816.822):
4-nitro-N-{[4-({4-nitro[(4-nitrophenyl)sulfonyl]anilino}-carbothioyl)-1-piperazinyl]carbothioyl}-N-(4-nitrophenyl)benzenesulfonamide.

The present invention is further illustrated by the following non-limiting experimental part.

Preparation of the Compounds of the Present Invention

All compounds having the general formula (III) were prepared in basically the same manner, viz by reacting a suitable isocyanate or isothiocyanate derivative with a suitable amine or amide derivative. This is illustrated by the preparation of B51, B48, B49, B641 and B674 as set forth hereinbelow.

Preparation of B51:
In a round bottomed flask, 4-cyanoaniline (0.01 mol) was dissolved in acetone (40 ml), followed by addition of an aqueous 10% KOH solution (5.6 g) and 4-nitrophenylisothiocyanate (1.8 g, 0.01 mol). The reaction mixture was refluxed for 4 h, after which the solvent was evaporated. Distilled water was then added, and the pH was adjusted to 7 by using aqueous 2N (or 20%) HCl, thus yielding a product precipitate, which was filtered off and dried in an oven at 40° C. Compound B51 was obtained in 66% yield as an orange powder.

Preparation of B48:
In a round bottomed flask, tetrahydrofurfurylamine (1.01 g, 0.01 mol, ρ=0.98) was mixed with acetone (40 ml), aqueous 10% KOH solution (5.6 g) and phenylisothiocyanate (1.36 g, 0.01 mol, p=1.13), after which the reaction mixture was refluxed until the reaction was completed. Then the solvent was evaporated, water added and the pH adjusted to 7 by using aqueous 2N HCl, thus yielding a product precipitate, which was filtered off and dried in an oven at 40° C. Compound B48 was obtained in 86% yield as an off-white powder.

Preparation of B49:
Phenylisothiocyanate (1.36 g, 0.01 mol) was reacted with 4-amino-3,5-diiodobenzoic acid (3.88 g, 0.01 mol) as described for B51, thus yielding B49 in 75% yield as a pale yellow powder.

Preparation of B641:
4-nitrophenylisocyanate (3.28 g, 0.02 mol) was reacted with 1,5-pentanediamine (1.02 g, 0.01 mol) as described for B51, thus giving B641 in 60% yield as a yellow powder.

Preparation of B674:

4-fluorobenzeneisothiocyanate (1.53 g, 0.01 mol) was reacted with N-(1-(2,6-diclorophenyl)-2-oxoethyl)-guanidine (2.46 g, 0.01 mol) as described for B48, thus giving B674 in 65% yield as a yellow powder.

The preparation of compounds having the general formula (IV) is normally performed in two reaction steps. Firstly, a suitable isocyanate or isothiocyanate derivative (1 eq.) is reacted with a suitable amine or amide derivative (1 eq.), whereby a disubstituted (thio)urea derivative is formed. Secondly, the disubstituted (thio)urea derivative is reacted with a suitable electrophile (2 eq.), whereby the desired tetrasubstituted (thio)urea derivative having the general formula (IV) is obtained. Typically, the preparation of compounds having the general formula (Iv) is performed in basically the same manner as in the following examples.

Preparation of B35-4:

4-nitrophenylisocyanate (1.8 g, 0.01 mol) and 2-amino-6-nitrobenzothiazole (4.57 g, 0.01 mol) were reacted as described for B51. The resulting intermediate product was then dissolved in N,N-dimethylformamide (DMF; 40 ml) and reacted with 2,5-dibromopyridine (4.73 g, 0.02 mol) in the presence of pyridine (2 ml). The reaction mixture was refluxed for 6 h, after which the DMF was evaporated and the residue was dissolved in 99% ethanol, after which the pH of the resulting solution was adjusted to 7 with aqueous 20% NaOH, whereby the product was precipitated. The precipitate was filtered off, washed with ethanol and dried in an oven at 40° C., thus giving B35-4 as a yellow powder in 55% yield.

Preparation of B42-37:

4-fluorobenzeneisothiocyanate (1.37 g, 0.01 mol) and 4-methylbenzenesulfonamide (1.87 g, 0.01 mol) were reacted as described for B51. The resulting intermediate product was then dissolved in DMF (70 ml) and reacted with 4-nitrobenzenesulfonylchloride (4.43 g, 0.02 mol) in the presence of pyridine (0.02 ml). The reaction mixture was refluxed for 6 h, and after work-up as described for B35-4, the product B42-37 was obtained as an orange powder in 63% yield.

Alternatively, a compound having the general formula (IV) may be prepared by derivatizing a commersially available disubstituted urea or thiourea derivative, e.g. Gliclazide, Glipizide, Gliquidone, Glisoxepid or Gluborid, with a suitable electrophile. Some examples of such derivatizations are the compounds B801 and B803-B808.

Compounds having the general formula (V) are typically prepared by reacting a suitable isocyanate or isothiocyanate derivative (1–2 eq.) with a suitable nitrogen containing cyclic compound (1 eq.) having at least one amine functionality. The obtained product (1 eq.) is then optionally treated with a suitable electrophile (2 eq.). The preparation of B45 and B46 illustrates the synthesis of this type of compounds. It also deserves to be mentioned that compounds having the general formula (V) are often symmetrical, i.e. have at least one element of symmetry.

Preparation of B45:

4-nitrophenylisothiocyanate (3.60 g, 0.02 mol) and piperazine (0.86 g, 0.01 mol) were reacted as described for B48 supra, thereby giving B45 as a red powder in 32% yield.

Preparation of B46:

B45 (4.47 g, 0.01 mol) was reacted with 4-nitrobenzenesulfonylchloride (4.43 g, 0.02 mol) as described for B35-4, thereby giving B46 as a white powder in 46% yield.

As an illustration, the structure of B46 is given hereinbelow:

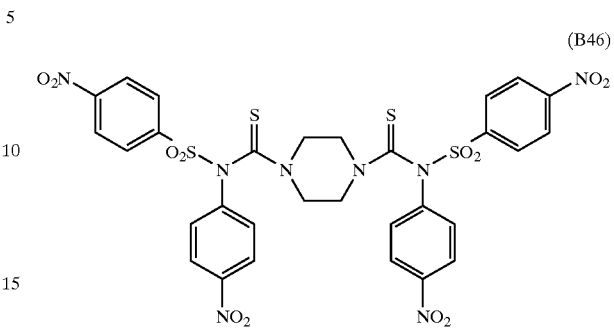

(B46)

As non-limiting examples of the present invention, typical suitable isocyanate or isothiocyanate derivatives used are butylisocyanate, 4-nitrophenylisothiocyanate, 4-nitrophenylisocyanate, 4-fluorophenylisothiocyanate, 4-fluorophenylisocyanate, phenylisothiocyanate, 3,5-diiodo-4-isothiocyanatobenzoic acid, cyclohexylisocyanate, 8-chloro-5-isothiocyanatoquinoline, 1,2-diiodo-3-isothiocyanatopropane, 3-chloro-4-isothiocyanatopyridine, 4-trifluoromethylbenzeneisothiocyanate and 2-hydroxy-4-isothiocyanatobenzoic acid.

As non-limiting examples of the present invention, typical suitable amine and amide derivatives used are 4-methylbenzenesulfonamide, 5-indanesulfonamide, 5-(dimethylamino)-1-naphthalenesulfonamhide, 1,1-dioxo-1,2,3,4-tetrahydro-1$\lambda^6$-thiochromene-7-sulfonamide, 7-fluoro-2,1,3-benzoxadiazole-4-sulfonamide, 3-chloro-4-pyridinamine, 2-amino-6-nitrobenzothiazole, 2-amino-4-nitrobenzothiazole, S-aminoisophthalic acid, 2-amino-5-nitrothiazole, 3,4,5-trimethoxyaniline, 2-chloro-4-pyrimidinamine, 4-isopropylaniline, 2-amino-4-methylthiazole, tetrahydrofurfurylamine, 4-amino-3,5-diiodobenzoic acid, glycine, 2,3-diiodo-1-propanamine, 4-aminobenzonitrile, 4-(2-aminoethyl)morpholine, 4-(aminomethyl)pyridine, 2-amino-5-[(4-nitrophenyl)sulphon-yl]thiazole, (2S,5R)-6-amino-3,3-dimethyl-7-oxo-4-thia-1-azabicyclo[3.2.0]heptane-2-carboxylic acid, 1-aminocyclopentanecarboxylic acid, 4-(aminomethyl)cyclohexanecarboxylic acid, 4-aminocyclohexanecarboxylic acid, 3-aminobenzoic acid, 2-trifluoromethyl-4-nitroaniline, 2-nitro-4-trifluoromethylaniline, 3-trifluoromethyl-4-chloroaniline, 2,3,6-trifluoro-5-aminobenzoic acid, 3,4,5-trifluorophenyl-2,5-dicyanoaniline, 3-chloro-2,5,6-trifluoro-4-pyridinamine, 2,2,2-trifluoroethylamine, 4-trifluoromethylaniline, 8-chloro-5-quinolinamine, (2-amino-5-iodophenyl)(phenyl)methanone, 2-amino-3-(4-iodophenyl)naphthaquinone, 4-iodophenylalanine, 4-amino-1-[3,4-dihydroxy-5-(hydroxy-methyl)tetrahydro-2-furanyl]-5-iodo-2(1H)-pyrimidone, 4-(4-hydroxy-3-iodophenoxy)-3,5-diiodophenylalanine, 4-hydroxy-3-iodophenylalanine, 2-iodo-2-aminobenzoic acid, 2-(6-amino-9H-purin-9-yl)-5-(iodomethyl)tetrahydro-3,4-furandiol, 4-amino-3,5,6-trichloro-2-pyridinecarboxylic acid, 3-amino-2-quinoxalinecarboxylic acid, 4-amino-2-quinolinecarboxylic acid, 4-amino-5-pyrimidinecarboxylic acid, 3-aminobicyclo[2.2.1]heptane-2-carboxylic acid, 2-amino-6-hydroxy-4-pyrimidinecarboxylic acid, 2-amino-5-chloro-4-pyrimidinecarboxylic acid, 1-amino-9,10-dioxo-9,10-dihydro-2-anthracenecarboxylic acid, 3-amino-1-adamantanecarboxylic acid, (1S,3R)-1-amino-1,3- cyclopentanedicarboxylic acid, 2-(ethylsulfanyl)-5-pyrimidinecarboxylic acid, 3-amino-1,1,3-propanetricarboxylic acid, 3-amino-2-pyrazinecarboxylic acid, 1-aminocyclopropanecarboxylic acid, 2-(1-(1-amino-2-oxoethyl)-2,3,4-trihydroxybutoxy)propanoic acid, 2-amino-6-((1S,2R)-1,2,3-trihydroxypropyl)-4(8H)-pteridone, 5-(2-aminoethyl)-1,2,4-benzenetriol, 5-amino-2,6-dioxo-1,2,3,6-tetrahydro-4-pyrimidinecarboxylic acid, 4-amino-1,3-dihydroxy-9,10-dioxo-8a,9,10,10a-tetrahydro-2-anthracenesulfonic acid, 2,4,5-trihydroxyphenylalanine, 6-amino-3-(3,4-dihydroxy-5-(hydroxymethyl)tetrahydro-2-furanyl)-4(3H)-pyrimidone, 4-((1S,1R)-2-amino-1-hydroxypropyl)-1,2-benzenediol, 4-(aminomethyl)-1,2-benzenediol, 4-amino-1-(3,4-dihydroxy-5-(hydroxymethyl)-tetrahydro-2-furanyl)-5-methyl-2(1H)-pyrimidone, 4-amino-1-(3,4-dihydroxy-5-(hydroxymethyl)tetrahydro-2-furanyl)-2(1H)-pyrimidinethione, 4-amino-1-(3,4-dihydroxy-5-(hydroxymethyl) tetrahydro-2-furanyl)-2(1R)-pyrimidone, 3,6-diamino-1,8-dihydroxy-dihydro-anthra-9,10-quinone, 4-(2-aminoethyl)-1,2-benzenediol, 4-(2-amino-1-hydroxyethyl)-1,2-benzenediol, 1-amino-1,3-cyclobutanedicarboxylic acid, (1R,3R)-1-amino-1,3-cyclopentanedicarboxylic acid, 2-(2-aminobenzoyl)benzoic acid, 6-aminonicotinic acid, 1-aminocyclohexanecarboxylic acid, 2-aminobicyclo[2.2.1]-heptane-2-carboxylic acid, 1,2-ethanediamine, 1,4-butanediamine, 1,4-benzenediamine, 1,5-pentanediamine, 4'-amino(1,1'-biphenyl)-4-ylamine, 2-amino-4,5-dihydroxy-pyrazine, 2-amino-4,5-pyrimidinediol, 4'-amino-3,3'-dichloro(1 μl-biphenyl)-4-ylamine, 4'-amino-3,3'-dimethyl(1,1'-biphenyl)-4-ylamine, $N^1,N^1$-diethyl-1,4-pentanediamine, 3,4-acridinediamine, 3,6-acridinediamine, 2,4-dibromo-6-([cyclohexyl(methyl)amino]methyl)aniline, 4-N,N-dimethylaminoaniline, 2-amino-6-chloropyrazine, 2-amino-6-chloropyridine, 2-amino-5-chloropyridine, 2-((Z)-(2,6-dichlorophenyl)methylidene)-1-hydrazinecarboximidamide, 2-{[amino(imino)methyl]amino}acetic acid, N-(2,3-dihydro-1,4-benzodioxin-2-ylmethyl)guanidine, N-(3-methyl-2-butenyl)guanidine, N-(1,4-dioxaspiro(4.5)dec-2-ylmethyl)guanidine, N-(1-(2,6-dichlorphenyl)-2-oxoethyl)guanidine, N-cyanoguanidine, guanidine, N-(3-{[amino(imino)methyl]amino}-2,4,5,6-tetrahydroxycyclohexyl)guanidine and 2-{(E)-3-(5-nitro-2-furyl)-1-((E)-2-(5-nitro-2-furyl)ethenyl)-2-propenylidene}-1-hydrazinecarboximidamide.

As non-limiting examples of the present invention, suitable electrophiles used are 2,5-dibromopyridine, 2,6-dibromopyridine, 2,3-dichloropyridine, 2,5-dichloropyrazine, 2,6-dichloropyrazine, 2-chloropyrazine, 2,6-dichloropyridine, 4-nitrobenzenesulfonylchloride, 4-fluorobenzenesulfonylchloride, benzenesulfonylchloride, trifluoromethylsulfonylchloride, 2-naphthalenesulfonylchloride and ethanesulfonylchloride.

By guidance of the examples above and known literature, e.g. U.S. Pat. No. 5,776,982, EP 0 015 110 and U.S. Pat. No. 4,486,439 as well as references cited therein, it is realized by a person skilled in the art that the preparation of the compounds according to the present invention is readily accomplished.

Biological Evaluation of the Present Compounds

The antiparasitic activity of the present compounds as prophylactic agents was evaluated in vivo on 100 one day old (1 day after hatch) chickens of Habbared X breed. The chickens were divided into five groups of 20 birds each, and each group was located in a separate pen (1 m×1 m). The chickens were then fed with unmedicated food up to day 7 after hatch. Fresh water was supplied ad libitum.

On day 8 after hatch, the five groups were given feed containing the following compounds (1 ppm=1 mg drug/kg feed):

Group #1: B49 (100 ppm);
Group #2: B42 (150 ppm);
Group #3: B46 (100 ppm);
Group #4: Coxistac (60 ppm), a known anticoccidial agent (see U.S. Pat. No. 3,857,948);
Group #5: no drug content (control group).

The chickens were fed as above on day 8 and 9 after hatch. On day 10 after hatch, each chicken was infected orally by 6 000-7 000 oocysts containing a mixture of 5 mature sporulated strains, namely E. acervulina, E. maxima, E. necatrix, E. tenella and E. brunetti. The groups #1–4 received drug as above from day 10 to 21 after hatch.

From day 14 to 21 after hatch, fresh fecal droplets were collected and examined daily. The average number of oocysts/g faeces was then calculated in accordance with the co-called Mc-Master technique (Soulsby, 1984). The final weight and mean total amount of consumed feed of each bird were also examined, and the results are summarized in Table 1 hereinbelow.

TABLE 1

Anticoccidial effect of B42, B46 and B49 on chicken of Habbared X breed

| Group (drug) | Average number of *Eimeria* spp. oocysts/g faeces | | | | | | | Mean body weight (g) | Mean amount of feed consumed (g) |
|---|---|---|---|---|---|---|---|---|---|
| | Day after hatch | | | | | | | | |
| | 14 | 15 | 16 | 17 | 18 | 19 | 21 | Total | |
| #1 (B49) | 0.0 | 3000 | 10000 | 20000 | 0.0 | 0.0 | 0.0 | 33000 | 66.0 | 95 |
| #2 (B42) | 0.0 | 0.0 | 3000 | 7000 | 0.0 | 0.0 | 0.0 | 10000 | 61.0 | 93 |
| #3 (B46) | 0.0 | 3000 | 14000 | 99000 | 6000 | 0.0 | 0.0 | 122000 | 54.5 | 39.3 |
| #4 (Coxistac) | 0.0 | 3000 | 4000 | 7000 | 2000 | 2000 | 0.0 | 18000 | 62.0 | 120 |
| #5 (no drug) | 0.0 | 15000 | 24000 | $1.3 \times 10^6$ | 174000 | 0.0 | 0.0 | $1.4 \times 10^6$ | 57.3 | 120 |

As can be seen from the total number of oocysts/g faeces in Table 1, the compounds B49 and B42 have an anticoccidial effect similar to that of Coxistac. But more importantly, the duration of the anticoccidial infection was also shorter in the chickens treated with B49 and B42 as compared to Coxistac. This was in turn manifested in the −20% lower amount of feed consumed in the groups treated with B49 and B42 as compared to both the Coxistac and the non-treated group. In any large scale breeding plant or operation, the properties of B49 and B42 should therefore be highly advantageous, since use thereof both reduces feeding costs and the amount of faeces without any loss of growth rate.

According to Table 1, the anticoccidial effect of B46 may at first seem inferior to that of Coxistac due to its comparatively higher total number of oocysts/g faeces. However, this is not the case, since the net result of using feed containing B46 is a fair body weight gain in combination with a surprisingly low feed intake. In fact, the feed consumption was ~67% lower in the B46 treated group in comparison with the Coxistac treated group. Since the body weight gain is still acceptable, this reduced feed consumption provides a considerable advantage in any large scale breeding plant or operation.

Moreover, the prophylactic anticoccidial effect of B42, B49 and B51 was also evaluated in chickens of Arbor Aker breed. These trials were conducted by using basically the same test protocol as that used for the chickens of Habbared X breed, albeit with the following modifications:
  i) On day 3 after hatch, the tested groups of chickens receieved feed containing 100 ppm of B42, B49, B51 or Coxistac (60 ppm);
  ii) On day 7 after hatch, the chickens were infected orally by oocysts containing a mixture of 8 mature sporulated strains, namely *E. mitis, E. hagani, E. praecox, E. acervulina, E. maxima, E. necatrix, E. tenella* and *E. brunetti*.

For B42 and B49, the results were essentially the same as those reported for the trials with the chickens of Habbared X breed (vide supra), whereas the results for B51 were comparable with those of B42.

In summary, it should be clear from this disclosure that the compounds according to the present invention are versatile new agents for antiparasitic treatment. Indeed, they are particularly suitable for treatment of coccidiosis and disorders related thereto, especially in poultry.

What is claimed is:

1. A compound having the general formula (I):

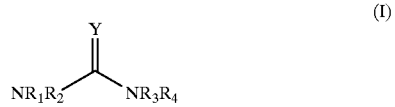

wherein
Y is selected from O and S;
$R_1$ is selected from the group consisting of 4-chloro-3-trifluoromethyl phenyl, N-hexahydrocyclopental[c] pyrrol-2(1H)-yl, 4-methylphenyl, 5-isophthalyl, 6-nitro-1,3-benzothiazol-2-yl, 4-(morpholino)ethyl, 4-cyanophenyl N-3-chloro-2,5,6-trifluoro-4-pyridinyl, 3-chloro-2,5,6-trifluoro-4-pyridinyl, 2,4,5-trihydroxyphenethyl, 3-carboxylphenyl, -3-(1adamantanecarboxylic acid), 2,3-dihydro-1H-inden-5-sulfonyl, 4-chlorophenyl, 3,4,5-trimethoxyphenyl, tetrahydro-2-furanylmethyl, 5-chloro-2-pyridinyl, 5-chloro-2-pyrazinyl, 4-carboxy-3-hydroxy-phenyl, 6-chloro-2-pyrazinyl, 4-fluorophenyl and 1-carboxycyclopentyl;

$R_2$ is selected from the group consisting of (4-fluorophenyl)sulfonyl, (4-nitrophenyl)sulfonyl, 2,2,2-trifluoroethyl, 2-naphtylsulfonyl, 5-bromo-2-pyridinyl, 6-chloro-2-pyrazinyl, and phenyl-sulfonyl;

$R_3$ is selected from the group consisting of (4-fluorophenyl)sulfonyl, (4-nitrophenyl)sulfonyl, 6-chloro-2-pyrazinyl, 2-naphtylsulfonyl, 5-bromo-2-pyridinyl, 4-cyanophenyl, and phenyl-sulfonyl; and $R_4$ is selected from the group consisting of 4-nitrophenyl, (4-nitrophenyl)sulfonyl, 4-fluorophenyl, 4-phthalyl, 8-chloro-5-quinolinyl, cyclohexyl, methyl-4-cyclohexancarboxylic acid, phenyl, 3,5-diiodo-4-carboxyphenyl.

2. A compound according to claim 1 wherein $R_2$ is equal to $R_3$.

3. A compound according to claim 1, wherein $NR_1R_2$ and $NR_3R_4$ are not identical.

4. A pharmaceutical composition comprising a compound according to claim 1 as active ingredient in association with a pharmaceutically acceptable adjuvant, diluent or carrier.

5. A pharmaceutical composition comprising a compound according to claim 2 as active ingredient in association with a pharmaceutically acceptable adjuvant, diluent or carrier.

6. A pharmaceutical composition comprising a compound according to claim 3 as active ingredient in association with a pharmaceutically acceptable adjuvant, diluent or carrier.

7. An animal feed, feed concentrate or drinking water comprising a compound according to claim 1.

8. An animal feed, feed concentrate or drinking water comprising a compound according to claim 2.

9. An animal feed, feed concentrate or drinking water comprising a compound according to claim 3.

10. A method for treatment of coccidiosis, wherein said method comprises administering to an animal of a therapeutically effective amount of a compound according to claim 1.

11. A method for treatment of coccidiosis, wherein said method comprises administering to an animal of a therapeutically effective amount of a compound according to claim 2.

12. A method for treatment of coccidiosis, wherein said method comprises administering to an animal of a therapeutically effective amount of a compound according to claim 3.

* * * * *